(12) United States Patent
Biemans et al.

(10) Patent No.: US 9,358,279 B2
(45) Date of Patent: *Jun. 7, 2016

(54) IMMUNOGENIC COMPOSITION

(71) Applicant: GLAXOSMITHKLINE BIOLOGICALS S.A., Rixensart (BE)

(72) Inventors: Ralph Leon Biemans, Rixensart (BE); Dominique Boutriau, Rixensart (BE); Carine Capiau, Rixensart (BE); Philippe Denoel, Rixensart (BE); Pierre Duvivier, Rixensart (BE); Jan Poolman, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/525,883

(22) Filed: Oct. 28, 2014

(65) Prior Publication Data

US 2015/0044253 A1 Feb. 12, 2015

Related U.S. Application Data

(63) Continuation of application No. 13/778,633, filed on Feb. 27, 2013, now Pat. No. 8,883,163, which is a continuation of application No. 11/917,726, filed as application No. PCT/EP2006/006220 on Jun. 23, 2006, now Pat. No. 8,398,983.

(30) Foreign Application Priority Data

| Jun. 27, 2005 | (GB) | .................. 0513069.5 |
| Jun. 27, 2005 | (GB) | .................. 0513071.1 |
| Jul. 28, 2005 | (GB) | .................. 0515556.9 |
| Nov. 28, 2005 | (GB) | .................. 0524204.5 |
| Dec. 21, 2005 | (GB) | .................. 0526040.1 |
| Dec. 21, 2005 | (GB) | .................. 0526041.9 |

(51) Int. Cl.

| A61K 39/385 | (2006.01) |
| A61K 39/102 | (2006.01) |
| A61K 39/095 | (2006.01) |
| A61K 39/116 | (2006.01) |
| C07H 3/00 | (2006.01) |
| A61K 39/05 | (2006.01) |
| A61K 39/08 | (2006.01) |
| A61K 39/09 | (2006.01) |
| A61K 39/02 | (2006.01) |
| A61K 39/29 | (2006.01) |
| A61K 39/00 | (2006.01) |
| A61K 39/12 | (2006.01) |

(52) U.S. Cl.
CPC ........... *A61K 39/102* (2013.01); *A61K 39/0017* (2013.01); *A61K 39/0018* (2013.01); *A61K 39/05* (2013.01); *A61K 39/08* (2013.01); *A61K 39/092* (2013.01); *A61K 39/095* (2013.01); *A61K 39/099* (2013.01); *A61K 39/116* (2013.01); *A61K 39/292* (2013.01); *C07H 3/00* (2013.01); *A61K 39/12* (2013.01); *A61K 2039/545* (2013.01); *A61K 2039/55* (2013.01); *A61K 2039/6037* (2013.01); *A61K 2039/627* (2013.01); *A61K 2039/70* (2013.01); *C12N 2730/10134* (2013.01); *C12N 2770/32634* (2013.01)

(58) Field of Classification Search
CPC .................................................... A61K 39/102
See application file for complete search history.

(56) References Cited

U.S. PATENT DOCUMENTS

| 4,057,685 A | 11/1977 | McIntire |
| 4,235,877 A | 11/1980 | Fullerton |
| 4,365,170 A | 12/1982 | Okuhara |
| 4,459,286 A | 7/1984 | Hilleman et al. |
| 4,673,574 A | 6/1987 | Anderson |
| 4,709,017 A | 11/1987 | Collier et al. |
| 4,727,136 A | 2/1988 | Jennings et al. |
| 4,808,700 A | 2/1989 | Anderson et al. |
| 4,950,740 A | 8/1990 | Greenfield et al. |
| 5,651,971 A | 7/1997 | Lees |
| 5,843,711 A | 12/1998 | Collier et al. |
| 5,849,301 A | 12/1998 | Lees |
| 5,869,058 A | 2/1999 | Cohen et al. |
| 5,917,017 A | 6/1999 | Collier et al. |
| 5,965,714 A | 10/1999 | Ryall |

(Continued)

FOREIGN PATENT DOCUMENTS

| CA | 2004810 | 6/1990 |
| CN | 1401328 | 3/2003 |

(Continued)

OTHER PUBLICATIONS

Choo, et al., Immunogenicity and reactogenicity of a group C meningococcal conjugate vaccine compared with a group A + C meningococcal polysaccharide vaccine in adolescents in a randomized observer-blind controlled trial, Vaccine 18:2686-2692 (2000).

(Continued)

*Primary Examiner* — Albert Navarro
(74) *Attorney, Agent, or Firm* — Barbara J. Carter

(57) ABSTRACT

The present application discloses an immunogenic composition comprising a Hib saccharide conjugate, at least one additional bacterial, for example *N. meningitidis*, saccharide conjugate(s), and a further antigen selected from the group consisting of whole cell pertussis and hepatitis B surface antigen, wherein the saccharide dose of the Hib saccharide conjugate is less than 5 µg.

1 Claim, No Drawings

(56) References Cited

U.S. PATENT DOCUMENTS

| | | | |
|---|---|---|---|
| 6,146,902 | A | 11/2000 | McMaster |
| 6,251,401 | B1 | 6/2001 | Ceccarini et al. |
| 6,455,673 | B1 | 9/2002 | Collier |
| 6,855,321 | B1 | 2/2005 | Rappuoli et al. |
| 7,018,637 | B2 | 3/2006 | Chong et al. |
| 7,122,191 | B2 | 10/2006 | Dominowski et al. |
| 7,348,006 | B2 | 3/2008 | Contorni et al. |
| 7,628,995 | B2 | 12/2009 | Bos et al. |
| 7,754,218 | B2 | 7/2010 | Contorni et al. |
| 7,838,014 | B2 | 11/2010 | Biemans et al. |
| 7,867,498 | B2 | 1/2011 | Rappuoli et al. |
| 7,939,087 | B2 | 5/2011 | Telford et al. |
| 8,007,807 | B2 | 8/2011 | Borkowski |
| 8,039,007 | B2 | 10/2011 | Rappuoli et al. |
| 8,062,641 | B2 | 11/2011 | Oscarson et al. |
| 8,192,746 | B2 | 6/2012 | Caulfield et al. |
| 8,221,770 | B2 | 7/2012 | Biemans et al. |
| 8,309,327 | B2 | 11/2012 | Biemans et al. |
| 8,329,184 | B2 | 12/2012 | Biemans et al. |
| 8,398,983 | B2 | 3/2013 | Biemans et al. |
| 8,409,587 | B2 | 4/2013 | Mayeresse et al. |
| 8,431,136 | B2 | 4/2013 | Biemans et al. |
| 8,574,596 | B2 | 11/2013 | Castado et al. |
| 8,679,770 | B2 | 3/2014 | De Vleeschauwer et al. |
| 8,703,148 | B2 | 4/2014 | Biemans et al. |
| 8,753,645 | B2 | 6/2014 | Biemans et al. |
| 8,753,651 | B2 | 6/2014 | Costantino |
| 8,758,764 | B2 | 6/2014 | Masignani et al. |
| 8,802,111 | B2 | 8/2014 | Contorni |
| 8,815,254 | B2 | 8/2014 | Biemans et al. |
| 8,883,163 | B2 * | 11/2014 | Biemans et al. ........... 424/184.1 |
| 8,883,166 | B2 | 11/2014 | Contorni et al. |
| 2003/0099672 | A1 | 5/2003 | Schultz |
| 2003/0180316 | A1 | 9/2003 | Boutriau et al. |
| 2004/0096461 | A1 | 5/2004 | Michon et al. |
| 2004/0126389 | A1 | 7/2004 | Berthet et al. |
| 2004/0202668 | A1 | 10/2004 | Boutriau et al. |
| 2004/0213804 | A1 | 10/2004 | Michon et al. |
| 2005/0019337 | A1 | 1/2005 | Ryall |
| 2005/0025780 | A1 | 2/2005 | Rubido et al. |
| 2005/0106181 | A1 | 5/2005 | Constantino |
| 2006/0121055 | A1 | 6/2006 | Campbell et al. |
| 2006/0121059 | A1 | 6/2006 | Garcon et al. |
| 2006/0166344 | A1 | 7/2006 | Pizza et al. |
| 2006/0257413 | A1 | 11/2006 | Zlotnick et al. |
| 2008/0199490 | A1 | 8/2008 | Biemans et al. |
| 2008/0260773 | A1 | 10/2008 | Del Giudice et al. |
| 2008/0305127 | A1 | 12/2008 | Poolman |
| 2009/0010959 | A1 | 1/2009 | Biemans et al. |
| 2009/0017059 | A1 | 1/2009 | Biemans et al. |
| 2009/0017072 | A1 | 1/2009 | Biemans et al. |
| 2009/0041802 | A1 | 2/2009 | Biemans et al. |
| 2009/0043077 | A1 | 2/2009 | Berti |
| 2009/0060945 | A1 | 3/2009 | Marshall |
| 2009/0136541 | A1 | 5/2009 | Biemans et al. |
| 2009/0162394 | A1 | 6/2009 | Biemans et al. |
| 2009/0214586 | A1 | 8/2009 | Contorni et al. |
| 2009/0252759 | A1 | 10/2009 | Biemans et al. |
| 2009/0311285 | A1 | 12/2009 | Biemans et al. |
| 2010/0060945 | A1 | 3/2010 | Asano |
| 2010/0074918 | A1 | 3/2010 | Poolman |
| 2010/0104593 | A1 | 4/2010 | Marshall |
| 2010/0143399 | A1 | 6/2010 | Biemans et al. |
| 2010/0183662 | A1 | 7/2010 | Biemans et al. |
| 2010/0203137 | A1 | 8/2010 | Contorni et al. |
| 2010/0209450 | A1 | 8/2010 | Biemans et al. |
| 2010/0215686 | A1 | 8/2010 | Biemans et al. |
| 2013/0122040 | A1 | 5/2013 | Blackkolb et al. |
| 2013/0216571 | A1 | 8/2013 | Ryall |

FOREIGN PATENT DOCUMENTS

| | | |
|---|---|---|
| CN | 1425465 | 6/2003 |
| CN | 1709505 | 12/2005 |
| EP | 0 161 188 | 11/1985 |
| EP | 0 208 375 | 1/1987 |
| EP | 0 211 258 | 2/1987 |
| EP | 0 378 881 | 7/1990 |
| EP | 0 427 347 | 5/1991 |
| EP | 0 471 177 | 2/1992 |
| EP | 0 477 508 | 4/1992 |
| EP | 0 497 524 | 8/1992 |
| EP | 0 497 525 | 8/1992 |
| EP | 0 594 610 | 5/1994 |
| EP | 0 594 950 | 5/1994 |
| EP | 0 941 738 | 9/1999 |
| EP | 1 946 769 | 7/2008 |
| WO | 91/01146 | 2/1991 |
| WO | 91/08772 | 6/1991 |
| WO | 93/15760 | 8/1993 |
| WO | 93/17712 | 9/1993 |
| WO | 93/24148 | 12/1993 |
| WO | 94/03208 | 2/1994 |
| WO | 95/08348 | 3/1995 |
| WO | 96/14086 | 5/1996 |
| WO | 96/29094 | 9/1996 |
| WO | 96/40242 | 12/1996 |
| WO | 97/00697 | 1/1997 |
| WO | 97/35613 | 10/1997 |
| WO | 98/42721 | 10/1998 |
| WO | 98/51339 | 11/1998 |
| WO | 98/58668 | 12/1998 |
| WO | 99/13906 | 3/1999 |
| WO | 99/42130 | 8/1999 |
| WO | 99/48525 | 9/1999 |
| WO | 00/10599 | 3/2000 |
| WO | 00/50006 | 8/2000 |
| WO | 00/56360 | 9/2000 |
| WO | 00/61761 | 10/2000 |
| WO | 01/00790 | 1/2001 |
| WO | 01/30390 | 5/2001 |
| WO | 01/41800 | 6/2001 |
| WO | 01/72337 | 10/2001 |
| WO | 02/00249 | 1/2002 |
| WO | 02/058737 | 8/2002 |
| WO | 02/080965 | 10/2002 |
| WO | 02/091998 | 11/2002 |
| WO | 03/007985 | 1/2003 |
| WO | 03/078453 | 9/2003 |
| WO | 03/080678 | 10/2003 |
| WO | 03/094834 | 11/2003 |
| WO | 03/094960 | 11/2003 |
| WO | 2004/011027 | 2/2004 |
| WO | 2004/020463 | 3/2004 |
| WO | 2004/032958 | 4/2004 |
| WO | 2004/048404 | 6/2004 |
| WO | 2004/067030 | 8/2004 |
| WO | 2004/067033 | 8/2004 |
| WO | 2004/083251 | 9/2004 |
| WO | 2004/103400 | 12/2004 |
| WO | 2004/110480 | 12/2004 |
| WO | 2005/000345 | 1/2005 |
| WO | 2005/020964 | 3/2005 |
| WO | 2005/032583 | 4/2005 |
| WO | 2005/089794 | 9/2005 |
| WO | 2005/105140 | 11/2005 |
| WO | 2006/075170 | 7/2006 |
| WO | 2006/097851 | 9/2006 |
| WO | 2007/000322 | 1/2007 |
| WO | 2007/000327 | 1/2007 |
| WO | 2007/000341 | 1/2007 |
| WO | 2007/000342 | 1/2007 |
| WO | 2007/000343 | 1/2007 |
| WO | 2008/011201 | 1/2008 |
| WO | 2008/081014 | 7/2008 |
| WO | 2008/081022 | 7/2008 |
| WO | 2008/135514 | 11/2008 |
| WO | 2008/149238 | 12/2008 |
| WO | 2009/016515 | 2/2009 |

(56) References Cited

OTHER PUBLICATIONS

De Bolle, et al., The length of a tetranucleotide repeat tract in Haemophilus influenzae determines the phase variation rate of a gene with homology to type III DNA methyltransferases, Molecular Microbiol 35(1): 211-222 (2000).
Fernandez, et al., Randomized Trial of the Immunogenicity of Fractional Dose Regimens of PRP-T Haemophilus Influenzae Type B Conjugate Vaccine, Am J Trop Med Hyg, 62(4):485-490 (2000).
Maclennan, et al., Safety, Immunogenicity, and Induction of Immunologic Memory by a Serogroup C Meningococcal Conjugate Vaccine in Infants, JAMA 283(21):2795-2801 (2000).
Perkins, New Opportunities for Prevention of Meningococcal Disease, JAMA 263(21):2842-2843 (2000).
Marketing Authorization Application for the Prevnar Pneumococcal Conjugate Vaccine, Wyeth Lederle Vaccines, S.A., (2000).
Richmond, et al., Safety and immunogenicity of a new Neisseria meningitidis serogroup C-tetanus toxoid conjugate vaccine in healthy adults, Vaccine 18:641-646 (2000).
Tan, Pneumococcal conjugate vaccines—implications for community antibiotic prescribing, Current Opinion in Microbiology 3:502-507 (2000).
Von Hunolstein, et al., Synthetic oligodeoxynocieotide containing CpG motif induces an anti-polysaccharide type 1-like immune response after immunization of mice with Haemophilus influenzae type b conjugate vaccine, Intl Immunol 12(3):295-303 (2000).
Announcement of Grant of Marketing Authorization for the Prevnar® Pneumococcal Conjugate Vaccine by EMEA—European Agency for the Evaluation of Medicinal Products (EMEA), CRMP/4130/00, Committee for Proprietary Medicinal Products European Public Assessment Report (EPAR) (2001).
Drachenberg, et al., A well-tolerated grass pollen-specific allergy vaccine containing a novel adjuvant, monophosphoryl lipid A, reduces allergic symptoms after only four preseasonal injections, Allergy 56: 498-505 (2001).
Falugi, et al., Rationally designed strings of promiscuous CD4+ T cell epitopes provide help to Haemophilus influenzae type b oligosaccharide: a model for new conjugate vaccines, Eur. J. Immunol., 31:3816-3824 (2001).
Rappuoli, Conjugates and reverse vaccinology to eliminate bacterial meningitis, Vaccine 19:2319-2322 (2001).
Rennels, et al., Safety and Immunogenicity of Combined Conjugate 9-Valent S. Pneumoniae-meningococcal group C (9vPnC-MnCC) and H. influenza b-9vPnC-MnCC (HbOC-9vPnC-MnCC) Vaccine, Abstract G02039, Abstracts of the 41st Interscience Conference of Antimicrobial Agents and Chemotherapy, Chicago (2001).
Richmond, et al., Evaluation of De-O-Acetylated Meningococcal C Polysaccharide-Tetanus Toxoid Conjugate Vaccine in Infancy: Reactogenicity, Immunogenicity, Immunologic Priming, and Bactericidal Activity against O-Acetylated and De-O-Acetylated Serogroup G Strains, Infect & Immun 69(4):2378-2382 (2001).
Romero-Siemer, et al., Functional Antibody Activity Elicited by Fractional Doses of Haemophilus influenzae Type b Conjugate Vaccine (Polyribosylribitol Phosphate-Tetanus Toxoid Conjugate), Clin Diagn Lab Immun 8(6):1115-1119 (2001).
Anderson, et al., Safety, Tolerability and Immunogenicity of Low Dose Haemophilus Influenzae Type b Conjugated to the Outer Membrane Protein Complex of Neisseria Meningitidis Group B, Pediatr Infect Dis J 21(4):350-352 (2002).
Berry, et al., Effect of O Acetylation of Neisseria meningitidis Serogroup A Capsular Polysaccharide on Development of Functional Immune Responses, Infect & Immun 70(7):3707-3713 (2002).
Burrage, et al., Effect of Vaccination with Carrier Protein on Response to Meningococcal C Conjugate Vaccines and Value of Different Immunoassays as Predictors of Protection, Infect & Immun 70(9):4946-4954 (2002).
Campbell, et al., Safety, Reactogencity, and Immunogenicity of a Tetravalent Meningococcal Polysaccharide-Diphtheria Toxoid Conjugate Vaccine Given to Healthy Adults, J Infect Dis 186:1848-1851 (2002).
Campbell, et al., Standard and alternative regimens of Haemophilus influenzae type b conjugate vaccine (polyribosylribitol phosphate-tetanus toxoid conjugate vaccine) elicit comparable antibody avidities in infants, Pediatric Infect Dis J. 21(9): 822-826 (2002).
Foster & Nadel, New therapies and vaccines for bacterial meningitis, Expert Opin Investig Drugs 11(8):1051-1060 (2002).
Lakshman and Finn, Meningococcal serogroup C conjugate vaccine, Expert Opin Biol Ther 2(1):87-96 (2002).
Nicol, et al., Haemophilus influenzae type b conjugate vaccine diluted tenfold in diphtheria-tetanus-whole cell pertussis vaccine: a randomized trial, Pediatr Infect Dis J 21(2):138-141 (2002).
Obaro, et al., Safety and immunogenicity of pneumococcal conjugate vaccine in combination with diphtheria, tetanus toxoid, pertussis and Haemophilus influenzae type b conjugate vaccine, Pediatr Infect Dis J 21(10):940-946 (2002).
Rennels, et al., Dose Escalation, Safety and Immunogenicity Study of a Tetravalent Meningococcal Polysaccharide Diphtheria Conjugate Vaccine in Toddlers, Pediatr Infect Dis J 21(10):978-979 (2002).
Ugozolli, et al., Combinations of Protein Polysaccharide Conjugate Vaccines for Intranasal Immunization, J Infect Dis 186:1358-1361 (2002).
Aristegui, et al., Comparison of the reactogenicity and immunogenicity of a combined diphtheria, tetanus, acellular pertussis, hepatitis B, inactivated polio (DTPa-HBV-IPV) vaccine, mixed with the Haemophilus influenzae type b (Hib) conjugate vaccine and administered as a single injection, with the DTPa-IPV/Hib and hepatitis B vaccines administered in two simultaneous injections to infants at 2, 4 and 6 month of age, Vaccine 21:3593-3600 (2003).
Vanlandschool et al., *Saccharomyces cerevisiae*-Derived HBsAg Preparations Differ in Their Attachment to Monocytes, Immune-Suppressive Potential, and T-Cell Immunogenicity, J Med Virol 70:513-519 (2003).
Zangwill, et al., Safety and immunogenicity of a heptavalent pneumococcal conjugate vaccine in infants, Vaccine 21:1894-1900 (2003).
Baraldo, et al., N19 Polyepitope as a Carrier for Enhanced Immunogenicity and Protective Efficacy of Meningococcal Conjugate Vaccines, Infect & Immun, 72(8):4884-4887 (2004).
Cai, et al., LC/MS Characterization of Meningococcal Depolymerizd Polysaccharide Group C Reducing Endgroup and Internal Repeating Unit, Anal Chem 76:7387-7390 (2004).
Chippaux, et al., Immunogenicity, safety, and memory of different schedules of Neisseria meningitidis A/C-diphtheria toxoid conjugate vaccine in infants in Niger, Vaccine 22:3303-3311 (2004).
Gatchalian, et al, Antibody persistence and immune memory in 10-month-old infants primed with Tritanrix™-HepB/Hib-MenAC at 6, 10, 14 weeks of age, Poster Session I Vaccinology, International Pathogenic Neisseria Conference (IPNC) Sep. 2004 SI-68 Poster & Abstract.
Gatchalian, et al., Immunogenicity and Safety of 3 doses of Tritanrix™-HepB/Hib-MenAC vaccine administered to infants at 6, 10 and 14 weeks of age, Poster Session I Vaccinology, International Pathogenic Neisseria Conference (IPNC) Sep. 2004 SI-69 Poster & Abstract.
Huebner, et al., Dose response of CRM197 and tetanus toxoid-conjugated Haemophilus influenzae type b vaccines, Vaccine 23(6): 802-806 (2004).
Zimmer & Stephens, Meningococcal conjugate vaccines, Expert Opin Pharmacother 5(4):855-863 (2004).
Buttery, et al., Immunogenicity and Safety of a Combination Pneumococcal-Meningococcal Vaccine in Infants, JAMA 293(14):1751-1758 (2005).
EMEA Guidelines on Adjuvants in Vaccines for Human Use, Infect & Immun 65:1710-1715 (2005).
Snape, et al., Meningococcal polysaccharide-protein conjugate vaccines, Lancet 5:21-30 (2005).
Tam, et al., Double-blind study comparing the immunogenicity of a licensed DTwPHib-CRM197 conjugate vaccine (Quattvaxem™) with three investigational, liquid formulations using lower doses of Hib-CRM197 conjugate, Vaccine, 23:1715-1719 (2005).
Borrow and Miller, Long-term protection in children with meningococcal C conjugate vaccination: lessons learned, Expert Review of Vaccines 5(6):851-857 (2006).

(56) References Cited

OTHER PUBLICATIONS

Conterno, et al., Cochrane database of systematic reviews, vol. 3, Abstract only (2006).
Girard, et al., A review of vaccine research and development: Meningococcal disease, Vaccine 24:4692-4700 (2006).
Nolan, et al., A novel combined Haemophilus influenzae type b-Neisseria meningitidis serogroups C and Y-tetanus-toxoid conjugate vaccine is immunogenic and induces immune memory when co-administered with DTPa-HBV-IPV and conjugate pneumococcal vaccines in infants, Vaccine 25:8487-8499 (2007).
Silveira, et al., Characterization and immunogenicity of meningococcal group C conjugate vaccine prepared using hydrazide-activated tetanus toxoid, Vaccine 25:7261-7270 (2007).
Bardotti, et al., Physiochemical characterisation of glycoconjugate vaccines for prevention of meningococcal diseases, Vaccine 26:2284-2296 (2008).
Gatchalian, et al., The development of a new heptavalent diphtheria-tetanus-whole cell pertussis-hepatitis B-Haemophilus influenzae type b-Neisseria meningitidis serogroups A and C vaccine: a randomized dose-ranging trial of the conjugate vaccine components, Intl J Infect Dis 12:278-288 (2008).
Frasch, Preparation of bacterial polysaccharide-protein conjugates: Analytical and manufacturing challenges, Vaccine 27:6468-6470 (2009).
Joshi, et al., Meningococcal polysaccharide vaccines: A review, Carbohydrate Polymers 75:553-565 (2009).
US Non-final Office Action dated Apr. 21, 2014 for U.S. Appl. No. 11/917,610.
GlaxoSmithKline's Oct. 21, 2014 Response to Non-final Office Action dated Apr. 21, 2014 for U.S. Appl. No. 11/917,610.
US Non-final Office Action dated Sep. 17, 2010 for U.S. Appl. No. 11/917,702.
GlaxoSmithKline's Feb. 17, 2011 Response to Non-final Office Action dated Sep. 17, 2010 for U.S. Appl. No. 11/917,702.
US Final Office Action dated Aug. 22, 2011 for U.S. Appl. No. 11/917,702.
GlaxoSmithKline's Request for Continued Examination with Amendment and IDS filed Feb. 22, 2012 for U.S. Appl. No. 11/917,702.
US Non-final Office Action dated Aug. 28, 2014 for U.S. Appl. No. 11/917,702.
US Non-final Office Action dated Dec. 22, 2011 for U.S. Appl. No. 11/917,709.
GlaxoSmithKline's Apr. 23, 2012 Response to Non-final Office Action dated Dec. 22, 2011 for U.S. Appl. No. 11/917,709.
US Notice of Non-compliant Amendment dated Apr. 26, 2012 for U.S. Appl. No. 11/917,709.
GlaxoSmithKline's May 3, 2012 Response to Notice of Non-compliant Amendment dated Apr. 26, 2012 for U.S. Appl. No. 11/917,709.
US Final Office Action dated Sep. 11, 2012 for U.S. Appl. No. 11/917,709.
GlaxoSmithKline's Mar. 11, 2013 Request for Continued Examination with Amendment and IDS filed for U.S. Appl. No. 11/917,709.
GlaxoSmithKline's Mar. 14, 2013 Petition to Revive Under 37 C.R.R. § 1.137(b) for U.S. Appl. No. 11/917,709.
US Decision to Grant dated Apr. 8, 2013 for GlaxoSmithKline's Mar. 14, 2013 Petition to Revive Under 37 C.R.R. § 1.137(b) for U.S. Appl. No. 11/917,709.
US Non-final Office Action dated Jan. 23, 2015 for U.S. Appl. No. 11/917,709.
EP Office Action dated Jun. 25, 2008 for EP application No. 06754599.6, publication No. EP1896063.
GlaxoSmithKline Nov. 7, 2008 Response to EP Office Action dated Jun. 25, 2008 for EP application No. 06754599.6, publication No. EP1896063.
EP Office Action dated Feb. 24, 2009 for EP application No. 06754599.6, publication No. EP1896063.
GlaxoSmithKline Jun. 2, 2009 Response to EP Office Action dated Feb. 24, 2009 for EP application No. 06754599.6, publication No. EP1896063.
EP Office Action dated Jan. 20, 2010 for EP application No. 06754599.6, publication No. EP1896063.
GlaxoSmithKline Feb. 3, 2010 Response to EP Office Action dated Jan. 20, 2010 for EP application No. 06754599.6, publication No. EP1896063.
EP Office Action dated Jun. 15, 2010 for EP application No. 06754599.6, publication No. EP1896063.
GlaxoSmithKline Oct. 18, 2010 Response to EP Office Action dated Jun. 15, 2010 for EP application No. 06754599.6, publication No. EP1896063.
EP Notice of Allowance dated Apr. 27, 2011 for EP application No. 06754599.6, publication No. EP1896063.
Pollabauer, et al., The influence of carrier protein on the immunogenicity of simultaneously administered conjugate vaccines in infants, Vaccine 27:1674-1679 (2009).
Dagan, et al., Glycoconjugate vaccines and immune interference: A review, Vaccine 28:5513-5523 (2010).
Ward, et al., Haemophilus Influenzae Vaccines, Chapter 12 of Vaccines, Second Edition, Plotkin & Mortimer Editors, pp. 337-386 (1994).
Lepow, Meningococcal Vaccines, Chapter 17 of Vaccines, Second Edition, Plotkin & Mortimer Editors, pp. 503-515 (1994).
Granoff, et al., Meningococcal Vaccines, Chapter 34 of Vaccines, Fourth Edition, Plotkin & Mortimer Editors, pp. 959-987 (1994).
Hiberix Consumer Medicine Information, GlaxoSmithKline 2011.
Third Party Observations by Anonymous filed Aug. 2004 with The European Patent Office, EP application No. 01960390.1, publication No. EP1296715.
Third Party Observations by Chiron (Novartis) filed Aug. 2004 with The European Patent Office, EP application No. 01960390.1, publication No. EP1296715.
Third Party Observations filed Mar. 2009 with The European Patent Office, EP application No. 06754610.1, publication No. EP1896064.
Third Party Observations filed Mar. 2009 with The European Patent Office, EP application No. 06762248.0, publication No. EP1896066.
Third Party Observations filed Mar. 2009 with The European Patent Office, EP application No. 06754582.2, publication No. EP1896061.
GSK Sep. 22, 2011 Reply to Third Party Observations filed Mar. 2009 with The European Patent Office, EP application No. 06754610.1, publication No. EP1896064.
Third Party Observations filed May 2010 with The European Patent Office, EP application No. 06754599.6, publication No. EP1896063.
Notice of Opposition by Sanofi Pasteur filed Dec. 30, 2010 against EP application No. 06754596.2, EP publication No. 1896062.
Notice of Opposition by Novartis filed Dec. 31, 2010 against EP application No. 06754596.2, EP publication No. 1896062.
Summons and Prelim Opinion dated Nov. 16, 2011 for EP application No. 06754596.2, EP publication No. 1896062.
GSK May 16, 2012 Response to Summons dated Nov. 16, 2011 for EP application No. 06754596.2, EP publication No. 1896062.
Novartis Apr. 16, 2012 Response to Summons dated Nov. 16, 2011 for EP application No. 06754596.2, EP publication No. 1896062.
Sanofi Pasteur Apr. 23, 2012 Response to Summons dated Nov. 16, 2011 for EP application No. 06754596.2, EP publication No. 1896062.
European Decision dated Jul. 17, 2012 on Oppositions filed by Sanofi Pasteur and Novartis Dec. 30-31, 2010, against EP application No. 06754596.2, EP publication No. 1896062.
Notice of Opposition by Crucell filed Aug. 23, 2012 against EP application No. 01960390.1, EP publication No. EP1296715.
Excerpt from European Office Action dated Jul. 8, 2008 for EP application No. 01960390.1, EP publication No. EP1296715—filed with Notice of Opposition by Crucell filed Aug. 23, 2012.
Notice of Opposition by Novartis filed Aug. 23, 2012 against EP application No. 01960390.1, EP publication No. EP1296715.
Notice of Opposition by Novartis filed Sep. 12, 2012 against EP application No. 06754599.6, EP publication No. 1896063.
GSK Apr. 12, 2013 Response to Sanofi Pasteur and Novartis Statement of Grounds of Appeal, EP Application No. 06754596.2, EP Publication No. 1896062.

(56) References Cited

OTHER PUBLICATIONS

Novartis Apr. 15, 2013 Response to GSK Appeal dated Dec. 5, 2012, EP Application No. 06754596.2, EP Publication No. 1896062.
GSK Apr. 22, 2013 Request for Oral Proceedings and Response to EP Communication dated Oct. 11, 2012 requesting patent proprietor's observations to the two Oppositions filed by Novartis and Crucell regarding EP Application No. 01960390.1, EP Publication No. 1296715.
GSK Apr. 29, 2013 Response to Novartis Opposition in EP Application No. 06754599.6, EP Publication No. 1896063.
US Non-final Office Action dated Jun. 21, 2010 for U.S. Appl. No. 11/917,569.
GlaxoSmithKline's Nov. 17, 2010 Response to Non-final Office Action dated Jun. 21, 2010 for U.S. Appl. No. 11/917,569.
US Notice of Allowance dated Apr. 20, 2011 for U.S. Appl. No. 11/917,569.
GlaxoSmithKline's Request for Continued Examination and IDS filed Jul. 19, 2011 for U.S. Appl. No. 11/917,569.
US Notice of Allowance dated Sep. 2, 2011 for U.S. Appl. No. 11/917,569.
GlaxoSmithKline's Request for Continued Examination with Amendment and IDS filed Dec. 2, 2011 for U.S. Appl. No. 11/917,569.
US Notice of Allowance dated Dec. 20, 2011 for U.S. Appl. No. 11/917,569.
GlaxoSmithKline's Request for Continued Examination with IDS filed Mar. 20, 2012 for U.S. Appl. No. 11/917,569.
US Notice of Allowance dated Feb. 22, 2013 for U.S. Appl. No. 11/917,569.
US Non-final Office Action dated Apr. 22, 2011 for U.S. Appl. No. 11/917,610.
GlaxoSmithKline's Jul. 23, 2011 Response to Non-final Office Action dated Apr. 22, 2011 for U.S. Appl. No. 11/917,610.
US Final Office Action dated Jan. 27, 2012 for U.S. Appl. No. 11/917,610.
GlaxoSmithKline's Request for Continued Examination with Amendment filed Feb. 28, 2012 for U.S. Appl. No. 11/917,610.
US Non-final Office Action dated Apr. 25, 2012 for U.S. Appl. No. 11/917,610.
GlaxoSmithKline's Jul. 25, 2012 Response to Non-final Office Action dated Apr. 25, 2012 for U.S. Appl. No. 11/917,610.
US Notice of Allowance dated Feb. 4, 2013 for U.S. Appl. No. 11/917,610.
GlaxoSmithKline's Feb. 22, 2013 Amendment under 37 C.F.R. § 1.312 for U.S. Appl. No. 11/917,610.
US Mar. 28, 2013 Response to GlaxoSmithKline's Feb. 22, 2013 Amendment under 37 C.F.R. § 1.312 for U.S. Appl. No. 11/917,610.
GlaxoSmithKline's Request for Continued Examination with IDS filed May 3, 2013 for U.S. Appl. No. 11/917,610.
GlaxoSmithKline's May 30, 2013 Supplemental Amendment under 37 C.F.R. § 1.312 for U.S Appl. No. 11/917,610.
Lowry, et al., Protein Measurement with the Folin Phenol Reagent, Department of Pharmacology, Washington University School of Medicine, St. Louis, Missouri (1951).
Uchida, et al., Diphtheria Toxin and Related Proteins, J Biological Chem, 248(11):3838-3844 (1973).
Peterson, Review of the Folin Phenol Protein Quantitation Method of Lowry, Rosebrough, Farr and Randall, Analytical Biochem, 100:201-220 (1979).
Bethell, et al., A Novel Method of Activation of Cross-linked Agaroses with 1,1'-Carbonyldiimidazole Which Gives a Matrix for Affinity Chromatography Devoid of Additional Charged Groups, J Biological Chem, 254(8):2572-2574 (1979).
Geyer, et al., Immunochemical Properties of Oligosaccharide-Protein Conjugates with Klebsiella-K2 Specificity, Med Microbial Immunol, 165:271-288 (1979).
Hearn, et al., Application of 1,1'-Carbonyldiimidazole-Activated Matrices for the Purification of Proteins, J Chromatography, 218:509-518 (1981).

Jennings and Lugowski, Immunochemistry of groups A, B and C meningococcal polysaccharide-tetanus toxoid conjugates, J Immunol 127(3):1011-1018 (1981).
Chu, et al., Further Studies on the Immunogenicty of Haemophilus influenzae Type b and Pneumococcal Type 6A polysaccharide-Protein Conjugates, Infect & Immun 40(1):245-256 (1983).
Schneerson, et al., Quantitative and Qualitative Analyses of Serum Antibodies Elicited in Adults by Haemophilus influenzae Type b and Pneumococcus Type 6A Capsular Polysaccharide-Tetanus Toxoid Conjugates, Infect & Immun 52(2):519-528 (1986).
Claesson, et al, Clinical and immunologic response to the capsular polysaccharide of Haemophilus influenzae type b alone or conjugated to tetanus toxoid in 18- to 23-month-old children, J Pediatr 112(5): 695-102 (1988).
Monsigny, et al., Colorimetric Determination of Neutral Sugars by a Resorcinol Sulfuric Acid Micromethod, Analytical Biochem, 175:525-530 (1988).
Takahashi, et al., Induction of CD8+ cytotoxic T cells by immunization with purified HIV-1 envelope protein in ISCOMs, Nature, 344:873-875 (1990).
Peeters, et al., Effect of carrier priming on immunogenicity of saccharide-protein conjugate vaccines, Infect & Immun 59(10):3504-3510 (1991).
Watemberg, et al., Safety and immunogenicity of Haemophilus type b-tetanus protein conjugate vaccine, mixed in the same syringe with diphtheria-tetanus-pertussis vaccine in young infants, Pediatr Infect Dis J 10(10):758-761 (1991).
Barrios, et al., Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming, Eur J Immunol 22(6):1365-1372 (1992).
Costantino, et al., Development and phase 1 clinical testing of a conjugate vaccine against meningococcus A and C, Vaccine 10(10):691-698 (1992).
Avendano, et al., Haemophilus influenzae type b polysaccharide-tetanus protein conjugate vaccine does not depress serologic responses to diphtheria, tetanus or pertussis antigens when coadministered in the same syringe with diphtheria-tetanus-pertussis vacine at two, four and six months of age, Pediatr Infect Dis J 12(8):638-643 (1993).
Barington, et al., Non-epitope-specific suppression of the antibody response to Haemophilus influenzae type b conjugate vaccines by preimmunization with vaccine components, Infect & Immun 61(2):432-438 (1993).
Anderson, et al., Safety and Immunogenicity of Meningococcal A and C Polysaccharide Conjugate Vaccine in Adults, Infect & Immun 62(8):3391-3395 (1994).
Barington, et al., Opposite effects of actively and passively acquired immunity to the carrier on responses of human infants to a Haemophilus influenzae type b conjugate vaccine, Infect & Immun 62(1):9-14 (1994).
Corbel, Control Testing of Combined Vaccines: A Consideration of Potential Problems and Approaches, Biologicals 22:353-360 (1994).
Van Der Meeren, et al., Phospholipid composition of r-DNA hepatitis B surface antigens, Intl J Pharmaceutics 106:89-92 (1994).
Agbarakwe, et al., Avidity of specific IgG antibodies elicited by immunisation against Haemophilus influenzae type b, J Clin Pathol 48:206-209 (1995).
Kuo, et al., Characterization of a Recombinant Pneumolysin and Its Use as a Protein Carrier for Pneumococcal Type 18C Conjugate Vaccines, Infect & Immun, 63(7):2706-2713 (1995).
Molrine, et al., Antibody Responses to Polysaccharide and Polysaccharide-Conjugate Vaccines after Treatment of Hodgkin Disease, Ann Intern Med 123:828-834 (1995).
Siber, et al., Development of a guinea pig model to assess immunogenicity of Haemophilus influenzae type b capsular polysaccharide conjugate vaccines. Vaccine 13(6):525-531 (1995).
AHFS Category 80:12, Haemophilus b Conjugate Vaccine (Tetanus Toxoid Conjugate) ActHIB® (1996).
Paradiso and Lindberg, Glycoconjugate Vaccines: Future Combinations, Dev Biol Stand 87:269-275 (1996).

(56) References Cited

OTHER PUBLICATIONS

Report of the Expert Panel VIII, European Commission COST/STD Initative—New Vaccines, Especially New Combined Vaccines, 14:691-700 (1996).
Sood, et al., Capsular polysaccharide-protein conjugate vaccines, Drug Discovery Today 1(9):381-387 (1996).
TETRAMUNE® Approved Data Sheet (1996).
Amir, et al., Immunogenicity and safety of a liquid combination of DT-PRP-T vs lyophilized PRP-T reconstituted with DTP, Vaccine 15(2):149-154 (1997).
Granoff, et al., Meningococcal Polysaccharide-Protein Conjugate Vaccines, Intl J Infect Dis 1:152-157 (1997).
Granoff, et al., MF59 Adjuvant Enhances Antibody Responses of Infant Baboons Immunized with Haemophilus influenzae Type b and Neisseria meningitidis Group C Oligosaccharide-CRM197 Conjugate Vaccine, Infect & Immun 65(5):1710-1715 (1997).
Mendelman, et al., Immunogenicity and safety of Haemophilus influenzae type b polysaccharide-Neisseria meningitidis conjugate vaccine in 7.5 ug liquid formulation: a comparison of three lots with the 15.0 ug lyophilized formulation, Vaccine 15(6/7): 775-781 (1997).
Zepp, et al., Evidence for induction of polysaccharide specific B-cell-memory in the 1st year of life: plain Haemophilus influenzae type b—PRP (Hib) boosters children primed with a tetanus-conjugate Hib-DTPa-HBV combined vaccine, Eur J Pediatr 156:18-24 (1997).
Bravo, et al., The New DTPw-HBV-Hib Combination Vaccine Can Be Used at the WHO Schedule with a Monovalent Dose of Hepatitis B Vaccine at Birth, Southeast Asian J Trop Med Public Health 29:772-778 (1998).
Dagan, et al., Reduced Response to Multiple Vaccines Sharing Common Protein Epitopes That Are Administered Simultaneously to Infants, Infect & Immun 66(5):2093-2098 (1993).
Gupta, et al., Biodegradable Polymer Microspheres as Vaccine Adjuvants and Delivery Systems, Dev Biol Stand 92:63-78 (1998).
Lagos, et al., Economisation of vaccination against Haemophilus influenzae type b: a randomized trial of immunogenicity of fractional-dose and two-dose regimens, Lancet 351:1472-1476 (1998).
Papaevangelou, Current combined vaccines with hepatitis B, Vaccine, 16(Supp):S69-S72 (1998).
Paradiso, Introduction to Combination Vaccines, Abstract S15, First Annual Conference on Vaccine Research, Washington (1998).
Rennels, et al., Safety and Immunogenicity of Heptavalent Pneumococcal Vaccine Conjugated to CRM197 in United States Infants, Pediatrics 101(4): 604-611 (1998).
Andre, Development and clinical application of new polyvalent combined paediatric vaccines, Vaccine 17:1620-1627 (1999).
Fattom, et al., Epitopic overload at the site of injection may result in suppression of the immune response to combined capsular polysaccharide conjugate vaccines, Vaccine 17:126-133 (1999).
Pines, et al., New acellular pertussis-containing paediatric combined vaccines, Vaccine, 17:1650-1656 (1999).
Poland, The burden of pneumococcal disease: the role of conjugate vaccines, Vaccine 17:1674-1679 (1999).
Richmond, et al., Meningococcal Serogroup C Conjugate Vaccine Is Immunogenic in Infancy and Primes for Memory, J. Infect Dis 179: 1569-1572 (1999).
Vaccines, 3rd Edition, edited by Plotkin & Orenstein, pp. 200-201 (1999).
Choo, et al., Immunogenicity and reactogenicity of a pneumococcal conjugate vaccine administered combined with a Haemophilus influenzae type b conjugate vaccine in United Kingdom infants, Pediatr Infect Dis J 19(9):854-862 (2000).
Pato, et al., Purification of capsular polysaccharide from Neisseria meningitidis serogroup C by liquid chromatography, J Chromatography B 832:262-267 (2006).
US Issue Notification dated Apr. 10, 2013 for U.S. Appl. No. 11/917,569.
US Final Office Action dated Jan. 29, 2015 for U.S. Appl. No. 11/917,610.
GlaxoSmithKline's Feb. 27, 2015 Response to US Non-final Office Action dated Aug. 28, 2014 for U.S. Appl. No. 11/917,702.
US Non-final Office Action dated Jun. 9, 2015 for U.S. Appl. No. 11/917,702.

\* cited by examiner

IMMUNOGENIC COMPOSITION

This application is a continuation application of U.S. application Ser. No. 13/778,633, filed Feb. 27, 2013 (to issue as U.S. Pat. No. 8,883,163 on Nov. 14, 2014), which is a continuation application of U.S. application Ser. No. 11/917,726, filed Dec. 14, 2007 (now U.S. Pat. No. 8,398,983, issued Mar. 19, 3013), pursuant to 35 U.S.C. §371 as a United States National Phase Application of International Patent Application Serial No. PCT/EP2006/006220 filed Jun. 23, 2006, which claims priority from Great Britain Application No. 0513069.5 filed in the United Kingdom on Jun. 27, 2005, from Great Britain Application No. 0513071.1 filed in the United Kingdom on Jun. 27, 2005, from Great Britain Application No. 0515556.9 filed in the United Kingdom on Jul. 28, 2005, from Great Britain Application No. 0524204.5 filed in the United Kingdom on Nov. 28, 2005, from Great Britain Application No. 0526040.1 filed in the United Kingdom on Dec. 21, 2005, and from Great Britain Application No. 0526041.9 filed in the United Kingdom on Dec. 21, 2005, the entire contents of each of which are hereby incorporated by reference.

The present application relates to immunogenic compositions and vaccines comprising a Hib saccharide conjugate and at least one additional bacterial saccharide conjugate(s) combined with further antigen(s) including whole cell pertussis and/or hepatitis B surface antigen, processes for making such immunogenic compositions and vaccines, and uses and methods of immunisation using the immunogenic composition and vaccine.

Bacterial polysaccharides have been shown to be effective immunogens for use in vaccines, particularly when conjugated to a carrier protein. Commercial conjugate vaccines are available against *Haemophilus influenzae* type b (Hibtiter® Wyeth-Lederle), pneumococcal polysaccharides (Prevnar®—Wyeth-Lederle) and meningococcal polysaccharides (Meningitec®—Wyeth-Lederle and Menactra®—Sanofi).

Immunogenic compositions and vaccines comprising a Hib conjugate, a *N. meningitidis* saccharide conjugate, whole cell pertussis and hepatitis B surface antigen have also been described. For instance WO 02/00249 discloses a seven valent immunogenic composition comprising a diphtheria toxoid, tetanus toxoid, whole cell pertussis, Hepatitis B surface antigen, Hib conjugate, MenA conjugate and MenC conjugate. The clinical trial results presented use a 5 µg saccharide dose of each of the bacterial saccharide conjugates.

The present invention concerns the provision of a combination vaccine comprising a Hib conjugate, an additional bacterial saccharide conjugate (for example an *N. meningitidis* saccharide conjugate) and further antigens including one or both of whole cell pertussis and Hepatitis B surface antigen. The saccharide doses used allow a good immune response to be generated against Hib and the additional bacterial saccharides as well as against the pertussis component and/or the Hepatitis B surface antigen component.

The inventors have surprisingly found that by reducing the saccharide dose of Hib and/or additional bacterial conjugates to below 5 µg per dose, in a combination vaccine comprising whole cell pertussis and/or Hepatitis B surface antigen, a good immune response to the saccharide conjugates is maintained and the immunogenicity of whole cell pertussis and Hepatitis B surface antigen is enhanced (for example such that the GMC for Pw and/or Hepatitis B as measured by ELISA is higher than the level achieved after immunisation with an immunogenic composition containing a 5 µg saccharide dose of each conjugate).

Accordingly, a first aspect of the invention provides an immunogenic composition comprising a Hib saccharide conjugate, at least one additional bacterial saccharide conjugate (s), and a further antigen selected from the group consisting of whole cell pertussis and hepatitis B surface antigen, wherein the saccharide dose of the Hib saccharide conjugate is less than 5 µg per dose.

DETAILED DESCRIPTION

The immunogenic composition of the invention comprises a Hib saccharide conjugate, and/or at least or exactly one, two, three or four bacterial saccharide conjugates, for example *N. meningitidis* saccharide conjugate(s), and a further antigen selected from the group consisting of whole cell pertussis and hepatitis B surface antigen, wherein the saccharide dose of the Hib saccharide conjugate is less than 5 µg or less than 4 µg, or between 1-4 µg or 1-3 µg, or 2-4 µg or 2-3 µg or around or exactly 2.5 µg and optionally the saccharide dose of the or each of the at least or exactly one, two, three or four additional bacterial saccharide conjugate(s) (for example *N. meningitidis* saccharide conjugate(s)) is less than 1-4 µg, 9 µg, 8 µg, 7 µg, 6 µg, 5 µg or 4 µg, or between 1-10 µg, 1-8 µg, 1-6 µg, 1-5 µg, 1-4 µg, 1-3 µg, or 2-4 µg or 2-3 µg or about or exactly 2.5 µg.

The term "saccharide" includes polysaccharides or oligosaccharides. Polysaccharides are isolated from bacteria or isolated from bacteria and sized to some degree by known methods (see for example EP497524 and EP497525) and optionally by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides.

The "saccharide dose" is measured in the amount of immunogenic composition or vaccine that is administered to a human.

A Hib saccharide is the polyribosyl phosphate (PRP) capsular polysaccharide or oligosaccharide of *Haemophilus influenzae* type b.

"At least one additional bacterial saccharide conjugate(s)" refers to a conjugate of any bacterial saccharide linked to a carrier protein. The bacterial saccharide is optionally a capsular saccharide derived from an *N. meningitidis* strain, a *S. pneumoniae* strain, an *S. typhi* strain, or any of the bacterial saccharides described herein.

"At least one *N. meningitidis* saccharide conjugate(s)" refers to *N. meningitidis* serogroup A capsular saccharide (MenA), *N. meningitidis* serogroup C capsular saccharide (MenC), *N. meningitidis* serogroup W135 capsular saccharide (MenW), to *N. meningitidis* serogroup Y capsular saccharide (MenY), *N. meningitidis* serogroup B capsular saccharide (MenB), serogroup C and Y capsular saccharides (MenCY), serogroup C and A capsular saccharides (MenAC), serogroup C and W135 capsular saccharides (MenCW), serogroup A and Y capsular saccharide (MenAY), serogroup A and W135 capsular saccharides (MenAW), serogroup W135 and Y capsular saccharides (Men WY), serogroup A, C and W135 capsular saccharide (MenACW), serogroup A, C and Y capsular saccharides (MenACY); serogroup A, W135 and Y capsular saccharides (MenAWY), serogroup C, W135 and Y capsular saccharides (MenCWY); or serogroup A, C, W135 and Y capsular saccharides (MenACWY), serogroup B and C capsular saccharides (MenBC), serogroup B, C and Y capsular saccharides (MenBCY), serogroup B, C and A capsular saccharides (MenABC), serogroup B, C and W capsular saccharides (MenBCW), serogroup A, B and Y capsular saccharide (MenABY), serogroup A, B and W capsular saccharides (MenABW), serogroup B, W135 and Y capsular saccharides (MenBWY), serogroup A, B, C and W135 capsular saccharide (MenABCW), serogroup A, B, C and Y capsular saccharides (MenABCY); serogroup A, B, W135 and Y capsular saccharides (MenABWY), serogroup B, C, W135 and Y capsular saccharides (MenBCWY); or serogroup A, B, C, W135 and Y capsular saccharides (MenABCWY).

For example, any of the combinations of N. meningitidis saccharide conjugates listed above, with or without the addition of Hib saccharide conjugate, may be present at a saccharide dose of less than 5 μg or less than 4 μg, or 1-4 μg or 1-3 μg, or 2-4 μg or 2-3 μg or around or exactly 2.5 μg.

"Around" or "approximately" are defined as within 10% more or less of the given figure for the purposes of the invention.

In an embodiment the saccharide dose of Hib can be the same as, more than or less than the saccharide dose of the N. meningitidis saccharide conjugate. The saccharide dose of the Hib saccharide conjugate is for example 100% or less than 90%, 80%, 75%, 70%, 60%, 50%, 40%, 30%, 20% or 10% of the mean or lowest saccharide dose of the at least one additional bacterial (for example N. meningitidis) saccharide conjugate(s). The saccharide dose of the Hib saccharide is for example between 20% and 60%, 30% and 60%, 40% and 60% or around or exactly 50% of the mean or lowest saccharide dose of the at least one additional bacterial (for example N. meningitidis) saccharide conjugate(s).

In an embodiment of the invention, the dose of the or each of the at least one additional bacterial (for example N. meningitidis) saccharides is the same, or approximately the same.

Examples of immunogenic compositions of the invention are compositions consisting of or comprising:

Examples of immunogenic compositions of the invention are compositions consisting of or comprising:

Hib conjugate and MenA conjugate and MenC conjugate, optionally at saccharide dose ratios of 1:2:2, 1:2:1, 1:4:2, 1:6:3, 1:3:3, 1:4:4, 1:5:5, 1:6:6 (w/w). Optionally, the saccharide dose of MenA is greater than the saccharide dose of MenC.

Hib conjugate and MenC conjugate and MenY conjugate, optionally at saccharide dose ratios of 1:2:2, 1:2:1, 1:4:2, 1:4:1, 1:8;4, 1:6:3, 1:3:3, 1:4:4, 1:5:5, 1:6:6 (w/w). Optionally, the saccharide dose of MenC is greater than the saccharide dose of MenY.

Hib conjugate and MenC conjugate and MenW conjugate, optionally at saccharide dose ratios of 1:2:2, 1:2:1, 1:4:2, 1:4:1, 1:8;4, 1:6:3, 1:3:3, 1:4:4, 1:5:5, 1:6:6 (w/w). Optionally the saccharide dose of MenC is greater than the saccharide dose of MenW.

Hib conjugate and MenA conjugate and MenW conjugate, optionally at saccharide dose ratios of 1:2:2, 1:2:1, 1:4:2, 1:4:1, 1:8;4, 1:6:3, 1:3:3, 1:4:4, 1:5:5, 1:6:6 (w/w). Optionally, the saccharide dose of MenA is greater than the saccharide dose of MenW.

Hib conjugate and MenA conjugate and MenY conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w). Optionally the saccharide dose of MenA is greater than the saccharide dose of MenY.

Hib conjugate and MenW conjugate and MenY conjugate, optionally at saccharide dose ratios of 1:2:2, 1:2:1, 1:1:2, 1:4:2, 1:2:4, 1:4:1, 1:1:4, 1:3;6, 1:1:3, 1:6:3, 1:3:3, 1:4:4, 1:5:5, 1:6:6 (w/w). Optionally the saccharide dose of MenY is greater than the saccharide dose of MenW.

The "further antigen" comprises one or both of whole cell pertussis (Pw) and Hepatitis B surface antigen (HepB). In an embodiment, the further antigen further comprises diphtheria toxoid (DT), tetanus toxoid (TT), acellular pertussis (Pa) and/or polio virus (IPV). In an embodiment, the further antigen comprises or consists of DT, TT and Pw. In an embodiment, the further antigen comprises or consists of DT, TT, pertussis antigen (Pa or Pw) and HepB. In an embodiment, the further antigen comprises or consists of DT, TT, pertussis antigen (Pa or Pw), HepB and IPV.

Hib and/or the N. meningitidis saccharide(s) included in the immunogenic compositions of the invention are conjugated to a carrier protein such as tetanus toxoid, tetanus toxoid fragment C, non-toxic mutants of tetanus toxin, diphtheria toxoid, CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711], pneumococcal pneumolysin, OMPC (meningococcal outer membrane protein—usually extracted from N. meningitidis serogroup B—EP0372501), synthetic peptides (EP0378881, EPO427347), heat shock proteins (WO 93/17712, WO 94/03208), pertussis proteins (WO 98/58668, EPO471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998) pneumolysin (Kuo et al (1995) Infect Immun 63; 2706-13), iron uptake proteins (WO 01/72337), toxin A or B of C. difficile (WO 00/61761) or Protein D (EP594610 and WO 00/56360).

In an embodiment, the immunogenic composition of the invention uses the same carrier protein (independently selected) in the Hib conjugate and the at least one N. meningitidis saccharide conjugate(s), optionally in the Hib conjugate and each of the N. meningitidis saccharide conjugates (optionally in all the saccharide conjugates present in the immunogenic composition).

In an embodiment, the immunogenic composition optionally comprises a Hib saccharide conjugate and MenA polysaccharide conjugate, a Hib saccharide conjugate and MenC saccharide conjugate, a Hib saccharide conjugate and MenW saccharide conjugate, a Hib saccharide conjugate and MenY saccharide conjugate, a Hib saccharide conjugate and MenA and MenC saccharide conjugates, a Hib saccharide conjugate and MenA and MenW saccharide conjugates, a Hib saccharide conjugate and MenA and MenY saccharide conjugates, a Hib saccharide conjugate and MenC and MenW saccharide conjugates, a Hib saccharide conjugate and MenC and MenY saccharide conjugates, a Hib saccharide conjugate and MenW and MenY saccharide conjugates, a Hib saccharide conjugate and MenA, MenC and MenW saccharide conjugates, a Hib saccharide conjugate and MenA, MenC and MenY saccharide conjugates, a Hib saccharide conjugate and MenA, MenW and MenY saccharide conjugates, a Hib saccharide conjugate and MenC, MenW and MenY saccharide conjugates or a Hib saccharide conjugate and MenA, MenC, MenW and MenY saccharide conjugates.

In an embodiment, a single carrier protein may carry more than one saccharide antigen (WO 04/083251). For example, a single carrier protein might be conjugated to Hib and MenA, Hib and MenC, Hib and MenW, Hib and MenY, MenA and MenC, MenA and MenW, MenA and MenY, MenC and MenW, MenC and MenY or Men W and MenY.

In an embodiment, the immunogenic composition of the invention comprises a Hib saccharide conjugated to a carrier protein selected from the group consisting of TT, DT, CRM197, fragment C of TT and protein D.

Where the carrier protein is TT or fragment thereof for Hib and the at least one *N. meningitidis* saccharide(s), the total dose of carrier is between 2.5-25 μg, 3-20 μg, 4-15 μg, 5-12.5 μg, 15-20 μg, 16-19 μg or 17-18 μg.

In an embodiment, the immunogenic composition of the invention comprises at least one, two, three or four *N. meningitidis* bacterial saccharide(s) conjugated to a carrier protein selected from the group consisting of TT, DT, CRM197, fragment C of TT and protein D.

The immunogenic composition of the invention optionally comprises a Hib saccharide conjugate having a ratio of Hib to carrier protein of between 1:5 and 5:1; 1:2 and 2:1; 1:1 and 1:4; 1:2 and 1:3.5; or around or exactly 1:2.5 or 1:3 (w/w).

The immunogenic composition of the invention optionally comprises at least one meningococcal saccharide (for example MenA and/or MenC and/or MenW and/or MenY) conjugate having a ratio of Men saccharide to carrier protein of between 1:5 and 5:1, between 1:2 and 5:1, between 1:0.5 and 1:2.5 or between 1:1.25 and 1:2.5 (w/w).

The ratio of saccharide to carrier protein (w/w) in a conjugate may be determined using the sterilized conjugate. The amount of protein is determined using a Lowry assay (for example Lowry et al (1951) J. Biol. Chem. 193, 265-275 or Peterson et al Analytical Biochemistry 100, 201-220 (1979)) and the amount of saccharide is determined using ICP-OES (inductively coupled plasma-optical emission spectroscopy) for MenA, DMAP assay for MenC and Resorcinol assay for MenW and MenY (Monsigny et al (1988) Anal. Biochem. 175, 525-530).

In an embodiment, the immunogenic composition of the invention the Hib saccharide is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH. Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685) glycosidic linkages (U.S. Pat. No. 4,673,574, U.S. Pat. No. 4,808,700) and 6-aminocaproic acid (U.S. Pat. No. 4,459,286).

The saccharide conjugates present in the immunogenic compositions of the invention may be prepared by any known coupling technique. For example the saccharide can be coupled via a thioether linkage. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. Optionally, the cyanate ester is coupled with hexane diamine or ADH and the amino-derivatised saccharide is conjugated to the carrier protein using heteroligation chemistry involving the formation of the thioether linkage, or is conjugated to the carrier protein using carbodiimide (e.g. EDAC or EDC) chemistry. Such conjugates are described in PCT published application WO 93/15760 Uniformed Services University and WO 95/08348 and WO 96/29094.

Other suitable techniques use carbiinides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction of with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid hydrazide (ADH) to the protein carrier by carbodiimide condensation (Chu C. et al Infect. Immunity, 1983 245 256), for example using EDAC.

In an embodiment, a hydroxyl group on a saccharide is linked to an amino or carboxylic group on a protein either directly or indirectly (through a linker). Where a linker is present, a hydroxyl group on a saccharide is optionally linked to an amino group on a linker, for example by using CDAP conjugation. A further amino group in the linker for example ADH may be conjugated to a carboxylic acid group on a protein, for example by using carbodiimide chemistry, for example by using EDAC. In an embodiment, the Hib or at least one *N. meningitidis* saccharide(s) is conjugated to the linker first before the linker is conjugated to the carrier protein.

In an embodiment, the Hib saccharide, where present, is conjugated to the carrier protein using CNBr, or CDAP, or a combination of CDAP and carbodiimide chemistry (such as EDAC), or a combination of CNBr and carbodiimide chemistry, (such as) EDAC. Optionally Hib is conjugated using CNBr and carbodiimide chemistry (optionally EDAC. For example, CNBr is used to join the saccharide and linker and then carbodiimide chemistry is used to join linker to the protein carrier.

In an embodiment, at least one of the at least one *N. meningitidis* saccharide(s) is directly conjugated to a carrier protein optionally Men W and/or MenY and/or MenC and/or MenA saccharide(s) is directly conjugated to a carrier protein. For example MenW; MenY; MenC; MenA; MenW and MenY; MenW and MenC; MenY and MenC; or MenW, MenY and MenC are directly linked to the carrier protein. Optionally at least one of the at least one *N. meningitidis* saccharide(s) is directly conjugated by CDAP. For example MenW; MenY; MenC; MenW and MenY; MenW and MenC; MenY and MenC; or MenW, MenY and MenC are directly linked to the carrier protein by CDAP (see WO 95/08348 and WO 96/29094).

Optionally the ratio of Men W and/or Y saccharide to carrier protein is between 1:0.5 and 1:2 (w/w) or the ratio of MenC saccharide to carrier protein is between 1:0.5 and 1:2 or 1:1.25 and 1:1.5 or 1:0.5 and 1:1 (w/w), especially where these saccharides are directly linked to the protein, optionally using CDAP.

In an embodiment, at least one *N. meningitidis* saccharide(s) is conjugated to the carrier protein via a linker, for instance a bifunctional linker. The linker is optionally heterobifunctional or homobifunctional, having for example a reactive amino group and a reative carboxylic acid group, 2 reactive amino groups or two reactive carboxylic acid groups. The linker has for example between 4 and 20, 4 and 12, 5 and 10 carbon atoms. A possible linker is ADH.

In an embodiment, MenA; MenC; or MenA and MenC is conjugated to a carrier protein via a linker.

In an embodiment, the *N. meningitidis* saccharide is conjugated to a carrier protein via a linker using CDAP and EDAC. For example, MenA; MenC; or MenA and MenC are conjugated to a protein via a linker (for example those with two amino groups at its ends such as ADH) using CDAP and EDAC as described above. For example, CDAP is used to conjugate the saccharide to a linker and EDAC is used to conjugate the linker to a protein. Optionally the conjugation via a linker results in a ratio of saccharide to carrier protein of of between 1:0.5 and 1:6; 1:1 and 1:5 or 1:2 and 1:4, for MenA; MenC; or MenA and MenC.

In an embodiment of the invention, the immunogenic composition comprises *N. meningitidis* capsular polysaccharides from at least one, two, three or four of serogroups A, C, W and Y conjugated to a carrier protein, wherein at least one, two, three or four or each *N. meningitidis* polysaccharide is either a native polysaccharide or is sized by a factor up to ×1.5, ×2, ×3, ×4, ×5, ×6, ×7, ×8, ×9, ×10 or ×20. For example, the average size of at least one, two, three or four or each *N. meningitidis* polysaccharide is above 50 kDa, 60 kDa, 75 kDa, 100 kDa, 110 kDa, 120 kDa or 130 kDa.

"Native polysaccharide" refers to a polysaccharide that has not been subjected to a process, the purpose of which is to reduce the size of the polysaccharide.

"Sized by a factor up to ×2" means that the polysaccharide is subject to a process intended to reduce the size of the polysaccharide but to retain a size more than half the size of the native polysaccharide. ×3, ×4 etc. are to be interpreted in the same way i.e. the polysaccharide is subject to a process intended to reduce the size of the polysaccharide but to retain a size more than a third, a quarter etc. the size of the native polysaccharide respectively.

In an aspect of the invention, the immunogenic composition comprises *N. meningitidis* capsular polysaccharides from at least one, two, three or four of serogroups A, C, W and Y conjugated to a carrier protein, wherein at least one, two, three or four or each *N. meningitidis* polysaccharide is native polysaccharide.

In an aspect of the invention, the immunogenic composition comprises *N. meningitidis* capsular polysaccharides from at least one, two, three or four of serogroups A, C, W and Y conjugated to a carrier protein, wherein at least one, two, three or four or each *N. meningitidis* polysaccharide is sized by a factor up to ×1.5, ×2, ×3, ×4, ×5, ×6, ×7, ×8, ×9 or ×10.

In an embodiment, the mean size of at least one, two, three, four or each *N. meningitidis* polysaccharide is between 50 KDa and 1500 kDa, 50 kDa and 500 kDa, 50 kDa and 300 KDa, 101 kDa and 1500 kDa, 101 kDa and 500 kDa, 101 kDa and 300 kDa as determined by MALLS.

In an embodiment, the MenA saccharide, where present, has a molecular weight of 50-500 kDa, 50-100 kDa, 100-500 kDa, 55-90 KDa, 60-70 kDa or 70-80 kDa or 60-80 kDa as determined by MALLS.

In an embodiment, the MenC saccharide, where present, has a molecular weight of 100-200 kDa, 50-100 kDa, 100-150 kDa, 101-130 kDa, 150-210 kDa or 180-210 kDa as determined by MALLS.

In an embodiment the MenY saccharide, where present, has a molecular weight of 60-190 kDa, 70-180 kDa, 80-170 kDa, 90-160 kDa, 100-150 kDa or 110-140 kDa, 50-100 kDa, 100-140 kDa, 140-170 kDa or 150-160 kDa as determined by MALLS.

In an embodiment the MenW saccharide, where present, has a molecular weight of 60-190 kDa, 70-180 kDa, 80-170 kDa, 90-160 kDa, 100-150 kDa, 110-140 kDa, 50-100 kDa or 120-140 kDa as determined by MALLS.

The molecular weights of the saccharide refers to the molecular weight of the polysaccharide measured prior to conjugation and is measured by MALLS.

In an embodiment the *N. meningitidis* saccharides are native polysaccharides or native polysaccharides which have reduced in size during a normal extraction process.

In an embodiment, the *N. meningitidis* saccharides are sized by mechanical cleavage, for instance by microfluidisation or sonication. Microfluidisation and sonication have the advantage of decreasing the size of the larger native polysaccharides sufficiently to provide a filterable conjugate.

In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0, 1.0-1.5, 1.0-1.2, 1.5-2.5, 1.7-2.2 or 1.5-2.0. All polydispersity measurements are by MALLS.

For MALLS analysis of meningococcal saccharides, two columns (TSKG6000 and 5000PWxl TOSOH Bioscience) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm).

In an embodiment, the MenA saccharide, where present is at least partially O-acetylated such that at least 50%, 60%, 70%, 80%, 90%, 95% or 98% of the repeat units are O-acetylated at least one position. O-acetylation is for example present at least at the O-3 position.

In an embodiment, the MenC saccharide, where present is at least partially O-acetylated such that at least 30%. 40%, 50%, 60%, 70%, 80%, 90%, 95% or 98% of ($\alpha$2→9)-linked NeuNAc repeat units are O-acetylated at least one or two positions. O-acetylation is for example present at the O-7 and/or O-8 position.

In an embodiment, the MenW saccharide, where present is at least partially O-acetylated such that at least 30%. 40%, 50%, 60%, 70%, 80%, 90%, 95% or 98% of the repeat units are O-acetylated at least one or two positions. O-acetylation is for example present at the O-7 and/or O-9 position.

In an embodiment, the MenY saccharide, where present is at least partially O-acetylated such that at least 40%, 50%, 60%, 70%, 80%, 90%, 95% or 98% of the repeat units are O-acetylated at least one or two positions. O-acetylation is present at the 7 and/or 9 position.

The percentage of O-acetylation refers to the percentage of the repeat units containing O-acetylation. This may be measured in the saccharide prior to conjugate and/or after conjugation.

A further aspect of the invention is a vaccine comprising the immunogenic composition of the invention and a pharmaceutically acceptable excipient.

Optionally, the immunogenic composition or vaccine contains an amount of an adjuvant sufficient to enhance the immune response to the immunogen. Suitable adjuvants include, but are not limited to, aluminium salts (aluminium phosphate or aluminium hydroxide), squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polphosphazene and derivatives, and immunostimulating complexes (ISCOMs) such as those described by Takahashi et al. (1990) Nature 344:873-875.

For the HibMen combinations discussed above, it may be advantageous for the Hib and Men saccharide conjugates not to be adsorbed to aluminium salt adjuvant or any adjuvant at all.

In an embodiment, the immunogenic composition is unadjuvanted. For the purpose of the invention, "unadjuvanted" means that an adjuvant component which is not an antigenic component in its own right is not present in the immunogenic composition.

In an embodiment of the invention HepB is adsorbed to aluminium phosphate (WO 93/24148).

In an embodiment, the immunogenic composition comprises a Hib saccharide conjugated to tetanus toxoid via a linker and MenC saccharide conjugated to tetanus toxoid either directly or through a linker and MenA saccharide conjugated to tetanus toxoid either directly or through a linker.

In an embodiment, the immunogenic composition of the invention is buffered at, or adjusted to, between pH 7.0 and 8.0, pH 7.2 and 7.6 or around or exactly pH 7.4.

The immunogenic composition or vaccines of the invention are optionally lyophilised in the presence of a stabilising agent for example a polyol such as sucrose or trehalose.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunizing dosages to be administered. Such factors are known in the vaccine art and it is well within the skill of immunologists to make such determinations without undue experimentation.

The active agent can be present in varying concentrations in the pharmaceutical composition or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application. Generally, it is expected that each dose will comprise 1-100 µg of protein antigen, optionally 5-50 µg or 5-25 µg. The vaccine preparations of the present invention may be used to protect or treat a mammal (for example a human patient) susceptible to infection, by means of administering said vaccine via systemic or mucosal route. A human patient is optionally an infant (under 12 months), a toddler (12-24, 12-16 or 12-14 months), a child (2-10, 3-8 or 3-5 years) an adolescent (12-25, 14-21 or 15-19 years) or an adult (any age over 12, 15, 18 or 21). These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effec-tively prevented, thus attenuating infection at its earliest stage). Although the vaccine of the invention may be administered as a single dose, components thereof may also be co-administered together at the same time or at different times (for instance if saccharides are present in a vaccine these could be administered separately at the same time or 1-2 weeks after the administration of a bacterial protein vaccine for optimal coordination of the immune responses with respect to each other). In addition to a single route of administration, 2 different routes of administration may be used. For example, viral antigens may be administered ID (intradermal), whilst bacterial proteins may be administered IM (intramuscular) or IN (intranasal). If saccharides are present, they may be administered IM (or ID) and bacterial proteins may be administered IN (or ID). In addition, the vaccines of the invention may be administered IM for priming doses and IN for booster doses.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

A further aspect of the invention is a vaccine kit for concomitant or sequential administration comprising two multivalent immunogenic compositions for conferring protection in a host against disease caused by Bordetella pertussis, Clostridium tetani, Corynebacterium diphtheriae, Haemophilus influenzae and Neisseria meningitidis. For example, the kit optionally comprises a first container comprising one or more of:

tetanus toxoid (TT),
diphtheria toxoid (DT), and
whole cell pertussis components and
optionally further comprising Hepatitis B surface antigen
and a second container comprising:
Hib saccharide conjugate, and
at least one, two, three or four N. meningitidis saccharide conjugate(s), wherein the saccharide dose of the Hib conjugate is less than 5 µg or 4 µg, or 1-4 µg or 1-3 µg, or 2-4 µg or 2-3 µg or around or exactly 2.5 µg and optionally the saccharide dose of the or each of the at least or exactly one, two, three or four additional bacterial saccharide conjugate(s) (for example N. meningitidis saccharide conjugate(s)) is less than 10 µg, 9 µg, 8 µg, 7 µg, 6 µg, 5 µg or 4 µg, or between 1-10 µg, 1-8 µg, 1-6 µg, 1-5 µg, 1-4 µg, 1-3 µg, or 2-4 µg or 2-3 µg or about or exactly 2.5 µg.

Examples of the Hib conjugate and the at least one additional bacterial saccharide (for example N. meningitidis saccharide) conjugate(s) are as described above. Any of the properties of the conjugates described above can be present in a vaccine kit.

Optionally, the vaccine kits of the invention comprise a third component. For example, the kit optionally comprises a first container comprising one or more of:

tetanus toxoid (TT),
diphtheria toxoid (DT), and
whole cell pertussis components and
optionally comprises Hepatitis B surface antigen;
and a second container comprising:
one or more conjugates of a carrier protein and a capsular saccharide from Streptococcus pneumoniae [where the capsular saccharide is optionally from a pneumococcal serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F].

and a third container comprising:
Hib saccharide conjugate, and
at least one *N. meningitidis* saccharide conjugate(s),
wherein the saccharide dose of the Hib conjugate is less than 5 µg or 4 µg, or 1-4 µg or 1-3 µg, or 2-4 µg or 2-3 µg or around or exactly 2.5 µg and optionally the saccharide dose of the or each of the at least or exactly one, two, three or four additional bacterial saccharide conjugate(s) (for example *N. meningitidis* saccharide conjugate(s)) is less than 10 µg, 9 µg, 8 µg, 7 µg, 6 µg, 5 µg or 4 µg, or between 1-10 µg, 1-8 µg, 1-6 µg, 1-5 µg, 1-4 µg, 1-3 µg, or 2-4 µg or 2-3 µg or about or exactly 2.5 µg.

Immunogenic compositions comprising meningococcal conjugates, for example HibMenC, HibMenAC, HibMenAW, HibMenAY, HibMenCW, HibMenCY, HibMenWY, MenAC, MenAW, MenAY, MenCW, MenCY, MenWY or MenACWY, including kits of similar composition to those described above, optionally comprise antigens from measles and/or mumps and/or rubella and/or varicella. For example, the meningococcal immunogenic composition contains antigens from measles, mumps and rubella or measles, mumps, rubella and varicella. In an embodiment, these viral antigens are optionally present in the same container as the meningococcal and/or Hib saccharide conjugate (s). In an embodiment, these viral antigens are lyophilised.

A further aspect of the invention is a process for making the immunogenic composition of the invention, comprising the step of mixing a Hib saccharide conjugate with at least one additional bacterial (for example *N. meningitidis*) saccharide conjugate(s) and a further antigen selected from the group consisting of whole cell pertussis and hepatitis B surface antigen to form a composition wherein the saccharide dose of the Hib conjugate is less than 5 µg or 4 µg, or between 1-4 µg or 1-3 µg, or 2-4 µg or 2-3 µg or around or exactly 2.5 µg and optionally the saccharide dose of the or each of the at least or exactly one, two, three or four additional bacterial (for example *N. meningitidis*) saccharide conjugate(s) is less than 10 µg, 8 µg, 7 µg, 6 µg, 5 µg or 4 µg, or between 1-10 µg, 1-8 µg, 1-6 µg, 1-5 µg, 1-4 µg, 1-3 µg, or 2-4 µg or 2-3 µg or about or exactly 2.5 µg.

A further aspect of the invention is a method of immunising a human host against disease caused by *Haemophilus influenzae* and optionally *N. meningitidis* infection comprising administering to the host an immunoprotective dose of the immunogenic composition or vaccine or kit of the invention.

A further aspect of the invention is an immunogenic composition of the invention for use in the treatment or prevention of disease caused by *Haemophilus influenzae* and/or *N. meningitidis*.

A further aspect of the invention is use of the immunogenic composition or vaccine or kit of the invention in the manufacture of a medicament for the treatment or prevention of diseases caused by *Haemophilus influenzae* and/or *N. meningitidis*.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLES

Example 1

Preparation of Polysaccharide Conjugates

The covalent binding of *Haemophilus influenzae* (Hib) PRP polysaccharide to TT was carried out by a coupling chemistry developed by Chu et al (Infection and Immunity 1983, 40 (1); 245-256). Hib PRP polysaccharide was activated by adding CNBr and incubating at pH10.5 for 6 minutes. The pH was lowered to pH8.75 and adipic acid dihyrazide (ADH) was added and incubation continued for a further 90 minutes. The activated PRP was coupled to purified tetanus toxoid via carbodiimide condensation using 1-ethyl-3-(3-dimethyl-aminopropyl)carbodiimide (EDAC). EDAC was added to the activated PRP to reach a final ratio of 0.6 mg EDAC/mg activated PRP. The pH was adjusted to 5.0 and purified tetanus toxoid was added to reach 2 mg TT/mg activated PRP. The resulting solution was left for three days with mild stirring. After filtration through a 0.45 µm membrane, the conjugate was purified on a sephacryl S500HR (Pharmacia, Sweden) column equilibrated in 0.2M NaCl.

MenC-TT conjugates were produced using native polysaccharides (of over 150 kDa as measured by MALLS) or were slightly microfluidised. MenA-TT conjugates were produced using either native polysaccharide or slightly microfluidised polysaccharide of over 60 kDa as measured by the MALLS method of example 2. MenW and MenY-TT conjugates were produced using sized polysaccharides of around 100-200 kDa as measured by MALLS (see example 2). Sizing was by microfluidisation using a homogenizer Emulsiflex C-50 apparatus. The polysaccharides were then filtered through a 0.2 µm filter.

Activation and coupling were performed as described in WO096/29094 and WO 00/56360. Briefly, the polysaccharide at a concentration of 10-20 mg/ml in 2M NaCl pH 5.5-6.0 was mixed with CDAP solution (100 mg/ml freshly prepared in acetonitrile/WFI, 50/50) to a final CDAP/polysaccharide ratio of 0.75/1 or 1.5/1. After 1.5 minutes, the pH was raised with sodium hydroxide to pH10.0. After three minutes tetanus toxoid was added to reach a protein/polysaccharide ratio of 1.5/1 for MenW, 1.2/1 for MenY, 1.5/1 for MenA or 1.5/1 for MenC. The reaction continued for one to two hours.

After the coupling step, glycine was added to a final ratio of glycine/PS (w/w) of 7.5/1 and the pH was adjusted to pH9.0. The mixture was left for 30 minutes. The conjugate was clarified using a 10 µm Kleenpak filter and was then loaded onto a Sephacryl S400HR column using an elution buffer of 150 mM NaCl, 10 mM or 5 mM Tris pH7.5. Clinical lots were filtered on an Opticap 4 sterilizing membrane. The resultant conjugates had an average polysaccharide:protein ratio of 1:1-1:5 (w/w).

In order to conjugate MenA capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 10 mg/ml solution of MenA was treated with a freshly prepared 100 mg/ml solution of CDAP in acetonitrile/water (50/50 (v/v)) to obtain a CDAP/MenA ratio of 0.75 (w/w). After 1.5 minutes, the pH was raised to pH 10.0. Three minutes later, ADH was added to obtain an ADH/MenA ratio of 8.9. The pH of the solution was decreased to 8.75 and the reaction proceeded for 2 hours.

Prior to the conjugation reaction, the purified TT solution and the $PSA_{AH}$ solution were diluted to reach a concentration of 10 mg/ml for $PSA_{AH}$ and 10 mg/ml for TT.

EDAC was added to the $PS_{AH}$ solution in order to reach a final ratio of 0.9 mg EDAC/mg $PSA_{AH}$. The pH was adjusted to 5.0. The purified tetanus toxoid was added with a peristaltic pump (in 60 minutes) to reach 2 mg TT/mg $PSA_{AH}$. The resulting solution was left 60 min at +25° C. under stirring to obtain a final coupling time of 120 min. The conjugate was clarified using a 10 μm filter and was purified using a Sephacryl S400HR column.

Example 2

Determination of Molecular Weight Using MALLS

Detectors were coupled to a HPLC size exclusion column from which the samples were eluted. On one hand, the laser light scattering detector measured the light intensities scattered at 16 angles by the macromolecular solution and on the other hand, an interferometric refractometer placed on-line allowed the determination of the quantity of sample eluted. From these intensities, the size and shape of the macromolecules in solution can be determined.

The mean molecular weight in weight ($M_w$) is defined as the sum of the weights of all the species multiplied by their respective molecular weight and divided by the sum of weights of all the species.

a) Weight-average molecular weight: -Mw- $$M_w = \frac{\sum W_i \cdot M_i}{\sum W_i} = \frac{m_2}{m_1}$$

b) Number-average molecular weight: -Mn- $$M_n = \frac{\sum N_i \cdot M_i}{\sum N_i} = \frac{m_1}{m_0}$$

c) Root mean square radius: -Rw- and $R^2w$ is the square radius defined by:

$$R^2 w$$

or $$(r^2)w = \frac{\sum m_i \cdot r_i^2}{\sum m_i}$$

(-$m_i$- is the mass of a scattering centre i and -$r_i$- is the distance between the scattering centre i and the center of gravity of the macromolecule).

d) The polydispersity is defined as the ratio -Mw/Mn-.

Meningococcal polysaccharides were analysed by MALLS by loading onto two HPLC columns (TSKG6000 and 5000PWxl TOSOH Bioscience) used in combination. 250 of the polysaccharide were loaded onto the column and was eluted with 0.75 ml of filtered water. The polysaccharides are detected using a light scattering detector (Wyatt Dawn DSP equipped with a 10 mW argon laser at 488 nm) and an inferometric refractometer Wyatt Otilab DSP equipped with a P100 cell and a red filter at 498 nm).

The molecular weight polydispersities and recoveries of all samples were calculated by the Debye method using a polynomial fit order of 1 in the Astra 4.72 software.

Example 3

Phase II Clinical Trial on HibMenAC-TT Conjugate Vaccine Mixed with DTPw-HepB

Study Design:

Open, randomized (1:1:1:1:1), single centre study with five groups. The five groups received the following vaccination regimen respectively, at 6, 10 and 14 weeks of age.

Tritanrix™-HepB/Hib-MenAC 2.5/2.5/2.5: henceforth referred to as 2.5/2.5/2.5

Tritanrix™-HepB/Hib-MenAC 2.5/5/5: henceforth referred to as 2.5/5/5

Tritanrix™-HepB/Hib-MenAC 5/5/5: henceforth referred to as 5/5/5

Tritanrix™-HepB+Hiberix™: henceforth referred to as Hiberix

Tritanrix™-HepB/Hiberix™+Meningitec™: henceforth referred to as Meningitec

Blood samples were taken at the time of the first vaccine dose (Pre) and one month after the third vaccine dose (Post-dose 3).

Tritanrix™ is a DTPw vaccine marketted by GlaxoSmith-Kline Biologicals S.A.

105 subjects were used in each of the five groups giving a total of 525 subjects in the study.

TABLE 1

| | Components per dose (0.5 ml) | | |
|---|---|---|---|
| | 2.5/2.5/2.5* | 2.5/5/5 | 5/5/5 |
| Hib capsular polysaccharide PRP conjugated to tetanus toxoid (TT) | 2.5 μg | 2.5 μg | 5 μg |
| *Neisseria meningitidis* A capsular polysaccharide (PSA) conjugated to TT | 2.5 μg | 5 μg | 5 μg |
| *Neisseria meningitidis* C capsular polysaccharide (PSC) conjugated to TT | 2.5 μg | 5 μg | 5 μg |

*The 2.5/2.5/2.5 vaccine was a dose dilution of GSK Biologicals' Hib-MenAC 5/5/5 vaccine containing 2.5 μg of each of PRP-TT, MenA-TT and MenC-TT.

The Hib-MenAC vaccine formulations were mixed extemporaneously with Tritanirix-HepB. GSK Biologicals' combined diphtheria-tetanus-whole cell *Bordetella pertussis*—hepatitis B (DTPw-HB) vaccine (Tritanrix-HepB) contains not less than 30 International Units (IU) of diphtheria toxoid, not less than 60 IU of tetanus toxoid, not less than 4IU of killed *Bordetella pertussis* and 10 μg of recombinant hepatitis B surface antigen.

Reference Therapy, Dose, Mode of Administration, Lot No.:

Vaccination Schedule/Site:

One group received Tritanrix.-HepB vaccine intramuscularly in the left thigh and Hiberix™ intramuscularly in the right thigh at 6, 10 and 14 weeks of age. Another group received Tritanrix™-HepB/Hiberix™ vaccine intramuscularly in the left thigh and Meningitec™ vaccine intramuscularly in the right thigh at 6, 10 and 14 weeks of age.

Vaccine/Composition/Dose/Lot Number:

The Tritanrix™-HepB vaccine used was as described above.

One dose (0.5 ml) of GSK Biologicals' *Haemophilus influenzae* type b conjugate vaccine: Hiberix™ contained 10 μg of PRP conjugated to tetanus toxoid. In the Hiberix Group, it was mixed with sterile diluent and in the Meningitec Group it was mixed with Tritanrix-HepB.

One dose (0.5 ml) of Wyeth Lederle's MENINGITEC™ vaccine contained: 10 μg of capsular polysaccharide of meningococcal group C conjugated to 15 μg of *Corynebacterium diphtheria* CRM197 protein and aluminium as salts.

Results—Immune Responses Generated Against Hib, MenA and MenC

TABLE 2a

Anti-PRP (μg/ml)

| Group | 2.5/2.5/2.5 | | | 2.5/5/5 | | | 5/5/5 | | | Hiberix ™ | | | Meningitec ™ | | |
|---|---|---|---|---|---|---|---|---|---|---|---|---|---|---|---|
| | % | 95% CL | | % | 95% CL | | % | 95% CL | | % | 95% CL | | % | 95% CL | |
| | GMC/T | LL | UL | GMC/T | LL | UL | GMC/T | LL | UL | GMC/T | LL | UL | GMC/T | LL | UL |
| % ≥0.15 | 100 | 96.5 | 100 | 99.0 | 94.8 | 100 | 100 | 96.5 | 100 | 100 | 96.5 | 100 | 100 | 96.5 | 100 |
| GMC | 20.80 | 15.96 | 27.10 | 22.62 | 17.72 | 28.88 | 19.36 | 15.33 | 24.46 | 38.55 | 29.93 | 49.64 | 10.94 | 8.62 | 13.88 |

TABLE 2b

SBA-MenC

| Group | 2.5/2.5/2.5 | | | 2.5/5/5 | | | 5/5/5 | | | Hiberix ™ | | | Meningitec ™ | | |
|---|---|---|---|---|---|---|---|---|---|---|---|---|---|---|---|
| | % | 95% CL | | % | 95% CL | | % | 95% CL | | % | 95% CL | | % | 95% CL | |
| | GMC/T | LL | UL | GMC/T | LL | UL | GMC/T | LL | UL | GMC/T | LL | UL | GMC/T | LL | UL |
| % ≥1:8 | 99 | 94.7 | 100 | 100 | 96.5 | 100 | 100 | 96.5 | 100 | 2.9 | 0.6 | 8.4 | 100 | 96.5 | 100 |
| GMT | 3132 | 2497 | 3930 | 4206 | 3409 | 5189 | 3697 | 3118 | 4384 | 4.7 | 3.9 | 5.6 | 4501 | 3904 | 5180 |

TABLE 2c

SBA MenA

| Group | 2.5/2.5/2.5 | | | 2.5/5/5 | | | 5/5/5 | | | Hiberix ™ | | | Meningitec ™ | | |
|---|---|---|---|---|---|---|---|---|---|---|---|---|---|---|---|
| | % | 95% CL | | % | 95% CL | | % | 95% CL | | % | 95% CL | | % | 95% CL | |
| | GMC/T | LL | UL | GMC/T | LL | UL | GMC/T | LL | UL | GMC/T | LL | UL | GMC/T | LL | UL |
| % ≥1:8 | 99.7 | 91.9 | 99.7 | 100 | 95.8 | 100 | 100 | 96.2 | 100 | 6.8 | 2.5 | 14.3 | 9.1 | 4.0 | 17.1 |
| GMT | 316.7 | 251.4 | 398.9 | 418.5 | 358.6 | 488.5 | 363 | 310.5 | 424.4 | 5.6 | 4.3 | 7.4 | 5.6 | 4.4 | 7.2 |

TABLE 2d

Anti-PSC (μg/ml)

| | 2.5/2.5/2.5 | | | 2.5/5/5 | | | 5/5/5 | | | Hiberix ™ | | | Meningitec ™ | | |
|---|---|---|---|---|---|---|---|---|---|---|---|---|---|---|---|
| | % | 95% CL | | % | 95% CL | | % | 95% CL | | % | 95% CL | | % | 95% CL | |
| Group | GMC/T | LL | UL | GMC/T | LL | UL | GMC/T | LL | UL | GMC/T | LL | UL | GMC/T | LL | UL |
| % ≥0.3 | 100 | 96.5 | 100 | 100 | 96.4 | 100 | 100 | 96.5 | 100 | 8.2 | 3.6 | 15.6 | 100 | 96.5 | 100 |
| GMC | 49.03 | 43.24 | 55.59 | 71.11 | 62.49 | 80.92 | 61.62 | 54.88 | 69.20 | 0.17 | 0.15 | 0.19 | 58.02 | 51.42 | 65.46 |

TABLE 2e

Anti-PSA (µg/ml)

| Group | 2.5/2.5/2.5 GMC/T | LL | UL | 2.5/5/5 GMC/T | LL | UL | 5/5/5 GMC/T | LL | UL | Hiberix™ GMC/T | LL | UL | Meningitec™ GMC/T | LL | UL |
|---|---|---|---|---|---|---|---|---|---|---|---|---|---|---|---|
| % ≥0.3 | 100 | 96.4 | 100 | 100 | 96.5 | 100 | 99.0 | 94.8 | 100 | 1.0 | 0.0 | 5.4 | 5.9 | 2.2 | 12.5 |
| GMC | 18.10 | 15.34 | 21.35 | 26.51 | 22.93 | 30.79 | 23.40 | 20.05 | 27.30 | 0.15 | 0.15 | 0.15 | 0.17 | 0.15 | 0.18 |

TABLE 2f

Anti-BPT (EL.U/ml)

| Group | 2.5/2.5/2.5 GMC/T | LL | UL | 2.5/5/5 GMC/T | LL | UL | 5/5/5 GMC/T | LL | UL | Hiberix™ GMC/T | LL | UL | Meningitec™ GMC/T | LL | UL |
|---|---|---|---|---|---|---|---|---|---|---|---|---|---|---|---|
| % VR | 100 | 96.4 | 100 | 98 | 93.1 | 99.8 | 94.2 | 87.8 | 97.8 | 100 | 96.3 | 100 | 99.0 | 94.7 | 100 |
| GMC | 108.2 | 94.4 | 123.9 | 81.4 | 70.5 | 94.0 | 60.1 | 51.0 | 70.8 | 110.2 | 96.1 | 126.3 | 86.7 | 75.4 | 99.7 |

TABLE 2g

Anti-HBs (mIU/ml)

| Group | 2.5/2.5/2.5 GMC/T | LL | UL | 2.5/5/5 GMC/T | LL | UL | 5/5/5 GMC/T | LL | UL | Hiberix™ GMC/T | LL | UL | Meningitec™ GMC/T | LL | UL |
|---|---|---|---|---|---|---|---|---|---|---|---|---|---|---|---|
| % ≥10 | 92.1 | 85.0 | 96.5 | 83.8 | 75.1 | 90.5 | 82.5 | 73.8 | 89.3 | 91.6 | 84.1 | 96.3 | 83.2 | 74.4 | 89.9 |
| GMC | 128.6 | 95.4 | 173.4 | 71.8 | 53.2 | 96.9 | 55.3.1 | 41.0 | 74.6 | 104.5 | 76.0 | 143.7 | 71.1 | 52.1 | 97.1 |

Conclusion

Tables 2f and 2g demonstrate that, when HibMenAC is mixed with DTPwHepB in a vaccine, a dose of 2.5/2.5/2.5 for Hib/MenA/MenC gives a higher immune response against pertussis toxoid and Hepatitis surface antigen than a dose of 2.5/5/5 which in turn generates a higher immune response against pertussis toxoid and Hepatitis B surface antigen than a dose of 5/5/5. Table 2a-e demonstrate that a low dose of HibMenA and MenC still achieves a good immune response against Hib, MenA and MenC with 99-100% of patients achieving an immune response above the chosen thresholds.

Example 4

HibMenAC Clinical Trial—Priming with HibMenAC Conjugates

A phase II, open, randomized study was carried out to assess the immune memory induced by primary vaccination course of Tritanrix™-HepB/HibMenAC vaccine, and to assess the immunogenicity and reactogenicity of a booster dose of GSK Biologicals' Tritanrix™-HepB vaccine mixed with either GSK Biologicals' Hib-MenAC conjugate vaccine or GSK Biologicals' $Hib_{2.5}$ vaccine at 15 to 18 months of age in subjects primed with Tritanrix™-HepB/Hib-MenAC. Five groups received the primary vaccination regimens at 6, 10 and 14 weeks of age as presented in table 3.

TABLE 3

| Primary vaccination | Grp | At 10 months of age | At 15 to 18 months of age |
|---|---|---|---|
| | | Treatment groups | |
| Tritanrix™-HepB/Hib-MenAC 2.5/2.5/2.5 | 1 | ⅕th dose of Mencevax™ AC (10 µg MenA & 10 µg MenC) and 10 µg of Plain PRP | Tritanrix™-HepB/$Hib_{2.5}$ |
| | 2 | — | Tritanrix™-HepB/$Hib_{2.5}$ |
| Tritanrix™-HepB/Hib-MenAC 5/5/5 | 3 | ⅕th dose of Mencevax™ AC (10 µg MenA & 10 µg MenC) and 10 µg of Plain PRP | Tritanrix™-HepB/$Hib_{2.5}$ |
| | 4 | — | Tritanrix™-HepB/$Hib_{2.5}$ |

TABLE 3-continued

| Primary vaccination | Grp | At 10 months of age | At 15 to 18 months of age |
|---|---|---|---|
| Tritanrix ™-HepB/Hib-MenAC 2.5/5/5 | 5 | 1/5th dose of Mencevax ™ AC (10 μg MenA & 10 μg MenC) and 10 μg of Plain PRP | Tritanrix ™-HepB/Hib$_{2.5}$ |
| | 6 | — | Tritanrix ™-HepB/Hib$_{2.5}$ |
| | | Control groups | |
| Tritanrix ™-HepB + Hiberix ™ | 7 | 1/5th dose of Mencevax ™ AC (10 μg MenA & 10 μg MenC) and 10 μg of Plain PRP | Tritanrix ™-HepB/Hib-MenAC |
| | 8 | — | Tritanrix ™-HepB/Hib-MenAC |
| Tritanrix ™-HepB/Hiberix ™ + Meningitec ™ | 9 | 1/5th dose of Mencevax ™ AC (10 μg MenA & 10 μg MenC) and 10 μg of Plain PRP | Tritanrix ™-HepB/Hib-MenAC |
| | 10 | — | Tritanrix ™-HepB/Hib-MenAC |

Blood samples were taken from Groups 1, 3, 5, 7 and 9 at the time of the plain polysaccharide (PS) booster (i.e. Pre-PS-Month 10) and one month after the plain polysaccharide booster (i.e. Post-PS-Month 11).

Note:

The immunogenicity results obtained in the five groups who received the plain polysaccharide booster (i.e. Groups 1, 3, 5, 7 and 9) have been presented.

Number of Subjects:

Planned: 450 (45 subjects per group)

Enrolled:

In Groups 1, 3, 5, 7 and 9 receiving the plain polysaccharide booster a total of 193 subjects (42 in Group 1, 39 in Group 3, 37 in Group 5, 36 in Group 7 and 39 in Group 9) were enrolled. Completed: Not applicable Immunogenicity:

Total enrolled cohort=193 subjects

Note:

In this study the total enrolled cohort=total vaccinated cohort.

Diagnosis and Criteria for Inclusion:

A male or female subject aged 10 months of age who had completed the three-dose primary vaccination course described in example 1, free of obvious health problems, who had not received previous booster vaccination against diphtheria, tetanus, pertussis, hepatitis B, meningococcal serogroups A or C and/or Hib disease since the study conclusion visit of the primary study. Written informed consent was obtained from the parent/guardian of the subject prior to study entry.

Study Vaccines, Dose, Mode of Administration, Lot No.:

All vaccines used in this study were developed and manufactured by GSK Biologicals.

Vaccination Schedule/Site:

Subjects in Groups 1, 3, 5, 7 and 9 received the combined polysaccharide A and polysaccharide C vaccine, 1/5th dose of Mencevax™ AC and 10 μg of plain PRP as an intramuscular injection in the left and right anterolateral thigh at 10 months of age, respectively.

Duration of Treatment:

The duration of the entire study was approximately 6 to 9 months per subject which included the booster vaccination administered at 15 to 18 months of age. Interim analysis was done at Month 11 (i.e. one month after administration of the plain polysaccharide booster at Month 10).

Criteria for Evaluation:

Prior to and one month after administration of the plain polysaccharide booster the criteria for evaluation for Groups 1, 3, 5, 7 and 9 were as follows SBA-MenA antibody titre≥1:8

SBA-MenC antibody titre≥1:8

Anti-PSA antibody concentration≥0.3 μg/ml

Anti-PSC antibody concentration≥0.3 μg/ml

Anti-PRP antibody concentration≥0.15 μg/ml.

Statistical Methods:

This interim analysis was based on the total enrolled cohort. All analyses were purely descriptive and no statistical inference on any endpoints was calculated. Analyses were performed only for the five groups (i.e. Groups 1, 3, 5, 7 and 9) that received the plain polysaccharide booster at 10 months of age. Though these five groups were sub-groups of the main groups in the primary study, the results are presented as per the primary study group allocation.

Analysis of Immunogenicity:

The results obtained at three time points have been presented in this example namely—one month after the third vaccine dose in the primary vaccination study (Example 1), prior to the administration of the polysaccharide booster (i.e. at 10 months of age) for evaluation of the persistence of immune response after primary vaccination and one month after the administration of the polysaccharide booster (i.e. at 11 months of age) for evaluation of immune memory induced by primary vaccination. At each time point: Geometric Mean antibody Concentrations or Titres (GMCs or GMTs) with 95% confidence intervals (CIs) were tabulated for serum bactericidal assay (SBA)-MenC, SBA-MenA, anti-PSC, anti-PSA and anti-PRP. Seropositivity or seroprotection rates with exact 95% CIs were calculated for each antibody. Antibody concentrations or titres prior to polysaccharide booster & one month post-polysaccharide booster were investigated using reverse cumulative curves (RCCs) for each antigen and serotype.

Results

Demography Results:

The mean age of the total enrolled cohort was 43.2 weeks with a standard deviation of 6.5 weeks. The male to female ratio was 1.3 (110/83). All subjects belonged to either the East Asian or South-East Asian race.

Immunogenicity Results:

The immunogenicity results for the total enrolled cohort are presented in the table 4.

TABLE 4

| Antibody | Group | Timing | | 95% CI (LL, UL) | | GMC/GMT | 95% CI (LL, UL) | |
|---|---|---|---|---|---|---|---|---|
| a | | | | | | | | |
| Anti-PRP (% ≥0.15 µg/ml) | 2.5/2.5/2.5 | PIII(M3) | 100.0 | 91.6 | 100.0 | 17.872 | 11.358 | 28.123 |
| | | PRE-PS | 97.5 | 86.8 | 99.9 | 6.940 | 4.402 | 10.941 |
| | | POST-PS | 100.0 | 91.6 | 100.0 | 66.510 | 38.690 | 114.334 |
| | 5/5/5 | PIII(M3) | 100.0 | 91.0 | 100.0 | 17.306 | 11.477 | 26.095 |
| | | PRE-PS | 94.9 | 82.7 | 99.4 | 4.520 | 2.946 | 6.937 |
| | | POST-PS | 100.0 | 91.0 | 100.0 | 44.418 | 26.595 | 74.186 |
| | 2.5/5/5 | PIII(M3) | 100.0 | 90.5 | 100.0 | 22.484 | 15.217 | 33.223 |
| | | PRE-PS | 100.0 | 89.7 | 100.0 | 5.092 | 3.290 | 7.883 |
| | | POST-PS | 100.0 | 90.5 | 100.0 | 54.244 | 32.251 | 91.234 |
| | Hiberix ™ | PIII(M3) | 100.0 | 90.3 | 100.0 | 30.106 | 18.316 | 49.485 |
| | | PRE-PS | 100.0 | 90.3 | 100.0 | 5.105 | 3.238 | 8.049 |
| | | POST-PS | 100.0 | 90.3 | 100.0 | 37.049 | 21.335 | 64.336 |
| | Meningitec ™ | PIII(M3) | 100.0 | 91.0 | 100.0 | 12.257 | 8.234 | 18.246 |
| | | PRE-PS | 100.0 | 91.0 | 100.0 | 4.227 | 2.804 | 6.372 |
| | | POST-PS | 100.0 | 91.0 | 100.0 | 24.354 | 15.308 | 38.747 |
| SBA-MenA (% ≥1:8) | 2.5/2.5/2.5 | PIII(M3) | 97.1 | 84.7 | 99.9 | 342.3 | 230.7 | 507.9 |
| | | PRE-PS | 91.7 | 77.5 | 98.2 | 161.9 | 93.9 | 279.1 |
| | | POST-PS | 100.0 | 88.4 | 100.0 | 737.2 | 577.3 | 941.4 |
| | 5/5/5 | PIII(M3) | 100.0 | 90.0 | 100.0 | 394.6 | 297.8 | 523.0 |
| | | PRE-PS | 94.3 | 80.8 | 99.3 | 193.2 | 126.7 | 294.7 |
| | | POST-PS | 96.7 | 82.8 | 99.9 | 720.8 | 479.8 | 1082.7 |
| | 2.5/5/5 | PIII(M3) | 100.0 | 90.0 | 100.0 | 385.8 | 285.9 | 520.5 |
| | | PRE-PS | 88.2 | 72.5 | 96.7 | 162.7 | 95.8 | 276.2 |
| | | POST-PS | 100.0 | 88.4 | 100.0 | 929.9 | 718.4 | 1203.6 |
| | Hiberix ™ | PIII(M3) | 10.0 | 2.1 | 26.5 | 6.6 | 3.7 | 11.7 |
| | | PRE-PS | 72.7 | 54.5 | 86.7 | 96.9 | 46.0 | 204.1 |
| | | POST-PS | 100.0 | 89.4 | 100.0 | 631.8 | 475.5 | 839.4 |
| | Meningitec ™ | PIII(M3) | 6.9 | 0.8 | 22.8 | 4.8 | 3.6 | 6.4 |
| | | PRE-PS | 80.0 | 63.1 | 91.6 | 119.7 | 62.7 | 228.3 |
| | | POST-PS | 92.1 | 78.6 | 98.3 | 449.9 | 271.7 | 745.0 |
| SBA-MenC (% ≥1:8) | 2.5/2.5/2.5 | PIII(M3) | 100.0 | 91.6 | 100.0 | 3342.3 | 2466.9 | 4528.3 |
| | | PRE-PS | 90.5 | 77.4 | 97.3 | 322.3 | 190.2 | 546.1 |
| | | POST-PS | 100.0 | 91.6 | 100.0 | 2713.5 | 1909.4 | 3856.2 |
| | 5/5/5 | PIII(M3) | 100.0 | 91.0 | 100.0 | 3863.1 | 3025.9 | 4932.1 |
| | | PRE-PS | 97.3 | 85.8 | 99.9 | 463.9 | 292.9 | 734.7 |
| | | POST-PS | 100.0 | 91.0 | 100.0 | 2377.3 | 1665.4 | 3393.4 |
| | 2.5/5/5 | PIII(M3) | 100.0 | 90.5 | 100.0 | 5339.0 | 3829.4 | 7443.6 |
| | | PRE-PS | 94.6 | 81.8 | 99.3 | 451.4 | 281.7 | 723.5 |
| | | POST-PS | 100.0 | 90.3 | 100.0 | 2824.7 | 2048.1 | 3895.8 |
| | Hiberix ™ | PIII(M3) | 2.8 | 0.1 | 14.5 | 4.5 | 3.6 | 5.7 |
| | | PRE-PS | 5.7 | 0.7 | 19.2 | 4.8 | 3.6 | 6.4 |
| | | POST-PS | 17.6 | 6.8 | 34.5 | 9.8 | 4.8 | 19.7 |
| | Meningitec ™ | PIII(M3) | 100.0 | 91.0 | 100.0 | 4557.8 | 3539.3 | 5869.5 |
| | | PRE-PS | 97.4 | 86.5 | 99.9 | 347.7 | 221.6 | 545.4 |
| | | POST-PS | 100.0 | 91.0 | 100.0 | 1557.7 | 1090.8 | 2224.4 |
| b | | | | | | | | |
| Anti-PSA (% ≥0.3 µg/ml) | 2.5/2.5/2.5 | PIII(M3) | 100.0 | 91.2 | 100.0 | 17.64 | 13.52 | 23.02 |
| | | PRE-PS | 92.5 | 79.6 | 98.4 | 1.79 | 1.22 | 2.62 |
| | | POST-PS | 100.0 | 91.6 | 100.0 | 23.58 | 16.76 | 33.17 |
| | 5/5/5 | PIII(M3) | 100.0 | 91.0 | 100.0 | 26.06 | 20.30 | 33.45 |
| | | PRE-PS | 97.4 | 86.5 | 99.9 | 2.25 | 1.60 | 3.18 |
| | | POST-PS | 100.0 | 91.0 | 100.0 | 24.13 | 17.64 | 33.01 |
| | 2.5/5/5 | PIII(M3) | 100.0 | 90.3 | 100.0 | 24.03 | 18.84 | 30.65 |
| | | PRE-PS | 91.2 | 76.3 | 98.1 | 1.47 | 0.99 | 2.19 |
| | | POST-PS | 100.0 | 90.5 | 100.0 | 22.68 | 15.81 | 32.54 |
| | Hiberix ™ | PIII(M3) | 0.0 | 0.0 | 10.3 | 0.15 | 0.15 | 0.15 |
| | | PRE-PS | 5.6 | 0.7 | 18.7 | 0.16 | 0.15 | 0.17 |
| | | POST-PS | 75.8 | 57.7 | 88.9 | 1.03 | 0.55 | 1.93 |
| | Meningitec ™ | PIII(M3) | 2.6 | 0.1 | 13.8 | 0.16 | 0.14 | 0.17 |
| | | PRE-PS | 7.7 | 1.6 | 20.9 | 0.16 | 0.15 | 0.18 |
| | | POST-PS | 66.7 | 49.8 | 80.9 | 0.84 | 0.49 | 1.42 |
| Anti-PSC (% ≥0.3 µg/ml) | 2.5/2.5/2.5 | PIII(M3) | 100.0 | 91.6 | 100.0 | 48.45 | 39.65 | 59.20 |
| | | PRE-PS | 100.0 | 91.2 | 100.0 | 7.11 | 5.69 | 8.89 |
| | | POST-PS | 100.0 | 91.2 | 100.0 | 21.55 | 17.24 | 26.94 |
| | 5/5/5 | PIII(M3) | 100.0 | 91.0 | 100.0 | 56.42 | 48.16 | 66.11 |
| | | PRE-PS | 100.0 | 91.0 | 100.0 | 8.32 | 6.74 | 10.28 |
| | | POST-PS | 100.0 | 90.0 | 100.0 | 22.32 | 18.21 | 27.36 |
| | 2.5/5/5 | PIII(M3) | 100.0 | 90.3 | 100.0 | 76.98 | 62.69 | 94.53 |
| | | PRE-PS | 100.0 | 89.7 | 100.0 | 8.64 | 6.93 | 10.77 |
| | | POST-PS | 100.0 | 90.5 | 100.0 | 24.75 | 19.37 | 31.61 |
| | Hiberix ™ | PIII(M3) | 6.1 | 0.7 | 20.2 | 0.16 | 0.15 | 0.18 |
| | | PRE-PS | 0.0 | 0.0 | 9.7 | 0.15 | 0.15 | 0.15 |
| | | POST-PS | 100.0 | 90.3 | 100.0 | 8.05 | 5.73 | 11.30 |

TABLE 4-continued

| Antibody | Group | Timing | 95% CI (LL, UL) | | GMC/GMT | 95% CI (LL, UL) | |
|---|---|---|---|---|---|---|---|
| | Meningitec ™ | PIII(M3) | 100.0 91.0 | 100.0 | 59.05 | 48.16 | 72.41 |
| | | PRE-PS | 100.0 91.0 | 100.0 | 7.33 | 5.51 | 9.75 |
| | | POST-PS | 100.0 90.7 | 100.0 | 17.13 | 13.38 | 21.94 |

95% CI: 95% confidence interval;
LL: Lower Limit;
UL: Upper Limit;
GMC/GMT: Geometric mean concentration/Geometric mean titre
PIII(M 3): Post-vaccination blood sample obtained one month after the third dose of the three-dose primary vaccination
PRE-PS: Blood sample obtained prior to plain polysaccharide booster at Month 10
POST-PS: Blood sample obtained one month after the plain polysaccharide booster Conclusion The HibMenAC 2.5/5/5 conjugate vaccine formulation containing a lower amount of Hib tended to give a better immune memory response to MenA and MenC in SBA assays than the vaccine formulations containing equal amounts of all three conjugates. This can be seen from a comparison of the POST-PS readings. Therefore the use of the 2.5/5/5 formulation in priming results in a superior immune memory response.

Looking at the PIII(M3) data, higher readings were seen for the 2.5/5/5 formulation for Hib (22.5 v 17) and MenC (76v 48 or 56 and 5339 v 3342 or 3863 by SBA).

Example 5a

Clinical Trial using HibMenCY given Concomitantly with Infanrix Penta and Prevenar in Infants at 2, 4 and 6 Months Study Design:

Phase II, open (partially double-blind*), randomized (1:1: 1:1:1), controlled, multicentric study with five parallel groups who received concomitant vaccines as follows as a 3-dose primary vaccination course at age 2, 4 and 6 months:

Group Hib-MenCY 2.5/5/5: Hib-MenCY (2.5/5/5)+Infanrix® penta+Prevenar®
Group Hib-MenCY 5/10/10: Hib-MenCY (5/10/10)+Infanrix® penta+Prevenar®
Group Hib-MenCY 5/5/5: Hib-MenCY (5/5/5)+Infanrix® penta+Prevenar®
Group Menjugate: Menjugate®+Act HIB®+Infanrix® penta**
Group ActHIB: ActHIB®+Infanrix® penta+Prevenar®

*Hib-MenCY (2.5/5/5) and Hib-MenCY (5/10/10) were administered in a double-blind manner. The Hib-MenCY (5/5/5) formulation could not be administered in a double blind as it was prepared by reconstituting a Hib-MenCY (10/10/10) formulation with 1.0 ml diluent (half the solution was discarded and the remaining 0.5 ml was administered), whereas the Hib-MenCY (2.5/5/5) and Hib-MenCY (5/10/ 10) formulations were administered after reconstitution with 0.5 ml diluent.

**Subjects from this group will be offered two doses of a licensed pneumococcal conjugate vaccine at the end of the booster study 792014/002 according to prescribing information.

Blood samples (4.0 ml) were obtained from all subjects prior to and one month after completion of the primary vaccination course (Study Month 0 and Study Month 5).

The study was planned to be on 400 subjects with 80 subjects in each of the five groups.

In study was completed with a total of 398 subjects (Group Hib-MenCY 2.5/5/5: 80 Group Hib-MenCY 5/10/10: 81; Group Hib-MenCY 5/5/5: 78; Group Menjugate: 81; Group ActHIB: 78)

Vaccination Schedule/Site:

Three doses injected intramuscularly at two month intervals, at approximately 2, 4 and 6 months of age as follows:

TABLE 5

| Vaccines administered and site | | |
|---|---|---|
| Group | Vaccines administered left thigh | Vaccines administered right thigh |
| Hib-MenCY 2.5/5/5 | Hib-TT (2.5 µg)-MenC-TT (5 µg)-MenY-TT (5 µg) | DTPa-HBV-IPV (Infanrix ® penta): upper Pneumococcal (Prevenar ®): lower |
| Hib-MenCY 5/10/10 | Hib-TT (5 µg)-MenC-TT (10 µg)-MenY-TT (10 µg) | DTPa-HBV-IPV (Infanrix ® penta): upper Pneumococcal (Prevenar ®): lower |
| Hib-MenCY 5/5/5 | Hib-TT (5 µg)-MenC-TT (5 µg)-MenY-TT (5 µg) | DTPa-HBV-IPV (Infanrix ® penta): upper Pneumococcal (Prevenar ®): lower |
| Menjugate ® | ActHIB ® | DTPa-HBV-IPV (Infanrix ® penta): upper MenC (Menjugate ®): lower |

TABLE 5-continued

Vaccines administered and site

| Group | Vaccines administered left thigh | Vaccines administered right thigh |
| --- | --- | --- |
| ActHIB ® | ActHIB ® | DTPa-HBV-IPV (Infanrix ® penta): upper<br>Pneumococcal (Prevenar ®): lower |

TABLE 6

Candidate vaccine formulation and lot numbers

| Vaccine | Formulation: contents/dose | Presentation | Lot no. (diluent lot no.) |
| --- | --- | --- | --- |
| Hib-MenCY 2.5/5/5 | *H. influenzae* type b capsular polysaccharide polyribosyl ribitol (PRP) 2.5 µg conjugated to tetanus toxoid (TT); *N. meningitidis* serogroup C capsular polysaccharide (PSC) 5 µg conjugated to TT; *N. meningitidis* serogroup Y capsular polysaccharide (PSY) 5 µg conjugated to TT | Lyophilized pellet in monodose vial (0.5 ml after reconstitution with saline diluent) | DCYH003A48 (01B20/22A) |
| Hib-MenCY 5/10/10 | PRP 5 µg conjugated to TT; PSC 10 µg conjugated to TT; PSY 10 µg conjugated to TT | Lyophilized pellet in monodose vial (0.5 ml after reconstitution with saline diluent) | DCYH002A48 (01B20/22A) |
| Hib-MenCY 5/5/5 | PRP 5 µg conjugated to TT; PSC 5 µg conjugated to TT; PSY 5 µg conjugated to TT | Lyophilized pellet in monodose vial.* | DCYH001A48 (01B20/22A) |

*The Hib-MenCY 5/5/5 was prepared by dissolving Hib-MenCY 10/10/10 formulation with 1.0 ml diluent; 0.5 ml was administered and the remaining 0.5 ml was discarded.

Criteria for Evaluation:

Immunogenicity: Measurement of titers/concentrations of antibodies against each vaccine antigen prior to the first dose (Month 0) and approximately one month after the third dose (Month 5) in all subjects. Determination of bactericidal antibody titers against *N. meningitidis* serogroups C and Y (SBA-MenC and SBA-MenY) by a bactericidal test (assay cut-offs: a dilution of 1:8 and 1:128) and ELISA measurement of antibodies against *N. meningitidis* serogroups C and Y (anti-PSC and anti-PSY, assay cut-offs ≥0.3 µg/ml and ≥2 µg/ml), the Hib polysaccharide PRP (anti-PRP, assay cut-offs ≥0.15 µg/ml and ≥1.0 µg/ml), the three pertussis antigens (anti-PT, anti-FHA, anti-PRN, assay cut-off ≥5 EL.U/ml), antibodies to hepatitis B surface antigen (anti-HBs, assay cut-off ≥10 mIU/mL), diphtheria and tetanus toxoids (anti-diphtheria and anti-tetanus, assay cut-off 0.1 IU/ml); anti-poliovirus types 1, 2 and 3 (assay cut-off 1:8); seven pneumococcal serotypes anti-4, anti-6B, anti-9V, anti-14, anti-18C, anti-19F, anti-23F (assay cut-off 0.05 µg/ml). Primary vaccine response to the pertussis antigens was defined as seropositivity (detectable antibodies) after the third dose in subjects with previously undetectable antibodies or at least maintenance of pre vaccination antibody concentration in subjects who were initially seropositive.

Safety (Criteria for evaluation): 8-day (Days 0 to 7) follow-up, after administration of each vaccine dose, of solicited local (pain, redness, swelling) and general (drowsiness, fever, irritability, and loss of appetite) symptoms reported on diary cards by the parent(s)/guardian(s) of the subjects; 31 day (Days 0 to 30) follow-up, after each vaccine dose, of unsolicited non-serious adverse events; and of serious adverse events (SAEs) during the entire study period.

Statistical Methods:

Immunogenicity

Geometric Mean antibody Concentrations or Titers (GMC/Ts) with 95% confidence intervals (CIs) were tabulated for each antigen. Calculation of GMC/Ts was performed by taking the anti-logarithm in base 10 (anti-log 10) of the mean of the log 10 concentration or titer transformations. Antibody concentrations or titers below the assay cut-off were given an arbitrary value of half the cut-off for the purpose of GMC/T calculation. Percentages of subjects with antibody concentration/titer above the specified assay cut-offs or with a vaccine response with exact 95% CI were calculated. Antibody concentrations/titers were investigated using reverse cumulative antibody curves for each antigen post-vaccination. The distribution of antibody concentration for the 7 pneumococcal antigens was tabulated.

The differences between the Hib-MenCY groups, compared with the control group were evaluated in an exploratory manner for each antibody, except for SBA-MenY and anti-PSY, in terms of (1) the difference between the control group (minus) the Hib-MenCY groups for the percentage of subjects above the specified cut-offs or with a vaccine response with their standardized asymptotic 95% Cl, (2) the GMC or GMT ratios of the control group over the Hib-MenCY groups with their 95% Cl. The control group was Menjugate for SBA-MenC and anti-PSC; the control group for all other antigens was Group ActHIB. The same comparisons were done to evaluate the difference between each pair of Hib-MenCY formulations for anti-PRP, SBA-MenC, anti-PSC, SBA-MenY, anti-PSY and anti-tetanus antibodies.

Seroprotection/Seropositivity Rates &GMC/Ts (ATP Cohort for Immunogenicity)

TABLE 7a

| | | | Anti-PRP (µg/ml) | | | | | | | |
|---|---|---|---|---|---|---|---|---|---|---|
| Group | N | % ≥0.15 | LL | UL | ≥1 | LL | UL | GMC | LL | UL |
| Hib MenCY 2.5/5/5 | 74 | 100.0 | 95.1 | 100.0 | 97.3 | 90.6 | 99.7 | 6.441 | 5.315 | 7.805 |
| Hib MenCY 5/10/10 | 76 | 100.0 | 95.3 | 100.0 | 98.7 | 92.9 | 100.0 | 7.324 | 5.877 | 9.127 |
| Hib MenCY 5/5/5 | 70 | 100.0 | 94.9 | 100.0 | 92.9 | 84.1 | 97.6 | 5.577 | 4.375 | 7.110 |
| Menjugate ™ | 74 | 98.6 | 92.7 | 100.0 | 89.2 | 79.8 | 95.2 | 4.465 | 3.399 | 5.865 |
| ActHIB ™ | 74 | 100.0 | 95.1 | 100.0 | 94.6 | 86.7 | 98.5 | 5.714 | 4.538 | 7.195 |

TABLE 7b

| | | | SBA-MenC (1/Dil) | | | | | | | |
|---|---|---|---|---|---|---|---|---|---|---|
| Group | N | % ≥1:8 | LL | UL | ≥1:128 | LL | UL | GMT | LL | UL |
| Hib MenCY 2.5/5/5 | 69 | 100.0 | 94.8 | 100.0 | 98.6 | 92.2 | 100.0 | 1293.1 | 1027.7 | 1627.1 |
| Hib MenCY 5/10/10 | 76 | 100.0 | 95.3 | 100.0 | 97.4 | 90.8 | 99.7 | 1065.6 | 858.8 | 1322.3 |
| Hib MenCY 5/5/5 | 72 | 100.0 | 95.3 | 100.0 | 95.8 | 88.3 | 99.1 | 968.4 | 770.8 | 1216.6 |
| Menjugate ™ | 74 | 100.0 | 95.1 | 100.0 | 98.6 | 92.7 | 100.0 | 1931.9 | 1541.2 | 2421.6 |
| ActHIB ™ | 76 | 1.3 | 0.0 | 7.1 | 0.0 | 0.0 | 4.7 | 4.2 | 3.8 | 4.5 |

TABLE 7c

| | | | Anti-PSC (µg/ml) | | | | | | | |
|---|---|---|---|---|---|---|---|---|---|---|
| Group | N | % ≥0.3 | LL | UL | ≥2 | LL | UL | GMC | LL | UL |
| Hib MenCY 2.5/5/5 | 63 | 100.0 | 94.3 | 100.0 | 98.4 | 91.5 | 100.0 | 12.02 | 9.90 | 14.59 |
| Hib MenCY 5/10/10 | 65 | 100.0 | 94.5 | 100.0 | 100.0 | 94.5 | 100.0 | 12.09 | 10.59 | 13.81 |
| Hib MenCY 5/5/5 | 61 | 100.0 | 94.1 | 100.0 | 98.4 | 91.2 | 100.0 | 9.95 | 8.34 | 11.87 |
| Menjugate ™ | 62 | 100.0 | 94.2 | 100.0 | 100.0 | 94.2 | 100.0 | 15.36 | 12.67 | 18.62 |
| ActHIB ™ | 63 | 1.6 | 0.0 | 8.5 | 0.0 | 0.0 | 5.7 | 0.15 | 0.15 | 0.16 |

TABLE 7d

| | | | SBA-MenY (1/Dil) | | | | | | | |
|---|---|---|---|---|---|---|---|---|---|---|
| Group | N | % ≥1:8 | LL | UL | ≥1:128 | LL | UL | GMT | LL | UL |
| Hib MenCY 2.5/5/5 | 67 | 98.5 | 92.0 | 100.0 | 95.5 | 87.5 | 99.1 | 843.5 | 640.1 | 1111.7 |
| Hib MenCY 5/10/10 | 68 | 100.0 | 94.7 | 100.0 | 97.1 | 89.8 | 99.6 | 1020.0 | 790.0 | 1316.8 |
| Hib MenCY 5/5/5 | 69 | 98.6 | 92.2 | 100.0 | 89.9 | 80.2 | 95.8 | 741.8 | 538.0 | 1022.9 |
| Menjugate ™ | 68 | 14.7 | 7.3 | 25.4 | 8.8 | 3.3 | 18.2 | 6.9 | 5.0 | 9.5 |
| ActHIB ™ | 74 | 16.2 | 8.7 | 26.6 | 9.5 | 3.9 | 18.5 | 7.3 | 5.2 | 10.1 |

TABLE 7e

| | | | Anti-PSY (µg/ml) | | | | | | | |
|---|---|---|---|---|---|---|---|---|---|---|
| Group | N | % ≥0.3 | LL | UL | ≥2 | LL | UL | GMC | LL | UL |
| Hib MenCY 2.5/5/5 | 67 | 100.0 | 94.6 | 100.0 | 100.0 | 94.6 | 100.0 | 19.22 | 15.42 | 23.95 |
| Hib MenCY 5/10/10 | 70 | 100.0 | 94.9 | 100.0 | 98.6 | 92.3 | 100.0 | 19.09 | 15.44 | 23.59 |
| Hib MenCY 5/5/5 | 72 | 100.0 | 95.0 | 100.0 | 97.2 | 90.3 | 99.7 | 15.83 | 12.64 | 19.82 |
| Menjugate ™ | 66 | 3.0 | 0.4 | 10.5 | 0.0 | 0.0 | 5.4 | 0.16 | 0.15 | 0.17 |
| ActHIB ™ | 69 | 0.0 | 0.0 | 5.2 | 0.0 | 0.0 | 5.2 | 0.15 | 0.15 | 0.15 |

Conclusion

The 2.5/5/5 and 5/10/10 formulations resulted in higher titres against Hib, MenC and MenY in terms of immunogenicity and SBA results. Therefore the inclusion of lower doses of Hib conjugate in a combined conjugate vaccine gave superior results.

Co-administration of Hib-MenCY with Infanrix penta and Prevenar™ gave satisfactory results Example 5b Effect of Co-Administration of HibMenCY with Prevenar™ on the Response to Pneumococcal Polysaccharides A further aspect of the study of example 3 was to investigate the level of antibodies raised against the 7 pneumococcal polysaccharides present in the Prevenar™ vaccine in order to assess the effect of co-administration of HibMenCY on the antibody titre raised against pneumococcal polysaccharides.

The GMCs and percentages of subjects with antibodies for the 7 pneumococcal serotypes ≥0.05 µg/ml and ≥0.2 µg/ml are shown in Table 8. Except for the 6B serotype, seropositivity rates for the 7vPn components ranged from 95.5-100% (antibody concentrations ≥0.05 µg/ml) and 93.9-100% (antibody concentrations ≥0.2 µg/ml) across groups. For the 6B serotype, seropositivity rates ranged from 88.4-98.6% (antibody concentrations ≥0.05 µg/ml) and 81.2-91.4% (antibody concentrations ≥0.2 µg/ml) across groups (ActHIB group: 92.3%≥0.05 µg/ml; 86.2%≥0.2 µg/ml).

TABLE 8a

| | | Anti-4 | | |
|---|---|---|---|---|
| Group | No. in group | % ≥0.05 µg/ml | % ≥0.2 µg/ml | GMC (µg/ml) |
| Hib-MenCY 2.5/5/5 | 69 | 100% | 100% | 2.101 |
| Hib-MenCY 5/10/10 | 70 | 100% | 100% | 2.049 |
| Hib-MenCY 5/5/5 | 69 | 100% | 100% | 2.023 |
| Menjugate ™ | 58 | 3.4% | 1.7% | 0.024 |
| ActHib ™ | 66 | 100% | 100% | 2.062 |

TABLE 8b

| | | Anti-6B | | |
|---|---|---|---|---|
| Group | No. in group | % ≥0.05 µg/ml | % ≥0.2 µg/ml | GMC (µg/ml) |
| Hib-MenCY 2.5/5/5 | 68 | 95.6% | 85.3% | 1.060 |
| Hib-MenCY 5/10/10 | 70 | 98.6% | 91.4% | 1.079 |
| Hib-MenCY 5/5/5 | 69 | 88.4% | 81.2% | 0.834 |
| Menjugate ™ | 63 | 4.8% | 1.6% | 0.027 |
| ActHib ™ | 65 | 92.3% | 86.2% | 0.879 |

TABLE 8c

| | | Anti-9V | | |
|---|---|---|---|---|
| Group | No. in group | % ≥0.05 µg/ml | % ≥0.2 µg/ml | GMC (µg/ml) |
| Hib-MenCY 2.5/5/5 | 68 | 100% | 100% | 3.102 |
| Hib-MenCY 5/10/10 | 71 | 98.6% | 97.2% | 2.363 |
| Hib-MenCY 5/5/5 | 71 | 100% | 100% | 2.823 |
| Menjugate ™ | 62 | 4.8% | 1.6% | 0.028 |
| ActHib ™ | 67 | 98.5% | 98.5% | 2.651 |

TABLE 8d

| | | Anti-14 | | |
|---|---|---|---|---|
| Group | No. in group | % ≥0.05 µg/ml | % ≥0.2 µg/ml | GMC (µg/ml) |
| Hib-MenCY 2.5/5/5 | 65 | 100% | 98.5% | 4.095 |
| Hib-MenCY 5/10/10 | 65 | 100% | 100% | 5.592 |
| Hib-MenCY 5/5/5 | 68 | 100% | 100% | 4.309 |
| Menjugate ™ | 49 | 49% | 14.3% | 0.062 |
| ActHib ™ | 65 | 100% | 98.5% | 4.372 |

TABLE 8e

| | | Anti-18C | | |
|---|---|---|---|---|
| Group | No. in group | % ≥0.05 µg/ml | % ≥0.2 µg/ml | GMC (µg/ml) |
| Hib-MenCY 2.5/5/5 | 67 | 98.5% | 98.5% | 3.518 |
| Hib-MenCY 5/10/10 | 71 | 100% | 98.6% | 2.969 |
| Hib-MenCY 5/5/5 | 72 | 100% | 100% | 2.936 |
| Menjugate ™ | 65 | 7.7% | 3.1% | 0.029 |
| ActHib ™ | 67 | 98.5% | 97% | 3.326 |

TABLE 8f

| | | Anti-19F | | |
|---|---|---|---|---|
| Group | No. in group | % ≥0.05 µg/ml | % ≥0.2 µg/ml | GMC (µg/ml) |
| Hib-MenCY 2.5/5/5 | 65 | 100% | 100% | 2.303 |
| Hib-MenCY 5/10/10 | 67 | 98.5% | 98.5% | 1.846 |
| Hib-MenCY 5/5/5 | 66 | 100% | 100% | 2.061 |
| Menjugate ™ | 56 | 12.5% | 3.6% | 0.030 |
| ActHib ™ | 65 | 100% | 96.9% | 1.881 |

TABLE 8g

Anti-23F

| Group | No. in group | % ≥0.05 µg/ml | % ≥0.2 µg/ml | GMC (µg/ml) |
|---|---|---|---|---|
| Hib-MenCY 2.5/5/5 | 66 | 98.5% | 97% | 2.581 |
| Hib-MenCY 5/10/10 | 68 | 97.1% | 94.1% | 2.112 |
| Hib-MenCY 5/5/5 | 70 | 95.7% | 95.7% | 2.098 |
| Menjugate ™ | 59 | 5.1% | 0.0% | 0.027 |
| ActHib ™ | 66 | 95.5% | 93.9% | 1.988 |

Conclusion

Co-administration of all three formulations of HibMenCY with Prevnar led to satisfactory immune responses against the seven pneumococcal serotypes. Serotype 6B is a difficult immunogen to raise a response against. In the case of 6B, a higher GMC and percentage of subjects achieving the two threshold levels was achieved using the lower Hib dose formulations of HibMenC. Therefore the uses of lower dose Hib conjugate vaccines for co-administration with pneumococcal polysaccharide conjugates leads to a better response against the 6B antigen.

Example 6

Phase II Clinical Trial Administering Hib MenCY Concomitantly with Infanrix Penta According to a 2, 3 and 4 Month Schedule Study Design:

A Phase II, open (partially double-blind*) randomized controlled multi-center study with 5 groups receiving a three-dose primary schedule with vaccines as follows:

Group Hib-MenCY 2.5/5/5: Hib-MenCY (2.5/5/5)+Infanrix™ penta

Group Hib-MenCY 5/10/10: Hib-MenCY (5/10/10)+Infanrix™ penta

Group Hib-MenCY 5/5/5: Hib-MenCY (5/5/5)+Infanrix™ penta

Group Hib-MenC: Hib-MenC (5/5)+Infanrix™ penta

Group Menjugate: Menjugate™**+Infanrix™ hexa (control).

*Hib-MenCY 2.5/5/5, Hib-MenCY 5/10/10 and Hib-MenC were administered in a double-blind manner while the Hib-MenCY 5/5/5 group and the Menjugate group were open.

**Menjugate™ was the vaccine that was administered to all subjects in the group. Vaccination at +/−2, 3, 4 months of age (StudyMonth 0, Month 1 and Month 2), and blood samples (3.5 ml) from all subjects prior to and one month post primary vaccination (StudyMonth 0 and Month 3).

Study Vaccine, Dose, Mode of Administration, Lot Number:

Three doses injected intramuscularly at one month intervals, at approximately 2, 3 and 4 months of age as follows:

TABLE 8

Vaccines administered (study and control), group, schedule/site and dose

| Group | Schedule (months of age) | Vaccine dose administered Site- Left upper thigh | Concomitant vaccine administered Site Right upper thigh |
|---|---|---|---|
| Hib-MenCY 2.5/5/5 | 2, 3, and 4 | Hib (2.5 µg)-MenC-TT (5 µg)-MenY-TT (5 µg) | DTPa-HBV-IPV (Infanrix ™ penta) |
| Hib-MenCY 5/10/10 | 2, 3, and 4 | Hib (5 µg)-MenC-TT (10 µg)-MenY-TT (10 µg) | DTPa-HBV-IPV (Infanrix ™ penta) |
| Hib-MenCY 5/5/5 | 2, 3, and 4 | Hib (5 µg)-MenC-TT (5 µg)-MenY-TT (5 µg) | DTPa-HBV-IPV (Infanrix ™ penta) |
| Hib-MenC | 2, 3, and 4 | Hib (5 µg)-Men C (5 µg) | DTPa-HBV-IPV (Infanrix ™ penta) |
| Menjugate ™ | 2, 3, and 4 | Menjugate ™ | DTPa-HBV-IPV/Hib (Infanrix ™hexa) |

Immunogenicity:

Measurement of antibody titres/concentrations against each vaccine antigen:

Prior to the first dose (Month 0) and approximately one month after the third dose (Month 3) in all subjects for: SBA-MenC and SBA-MenY, anti-PSC and anti-PSY, anti-PRP, anti-T, anti-FHA, anti-PRN and anti-PT. Using serum bactericidal activity against N. meningitidis serogroups C and Y (SBA-MenC and SBA-MenY cut-off: 1:8 and 1:128); ELISA assays with cut-offs: ≥0.3 µg/ml and 2 µg/ml for anti-N. meningitidis serogroups C and Y polysaccharides (anti-PSC IgG and anti-PSY IgG); ≥0.15 µg/ml and ≥1.0 µg/ml for Hib polysaccharide polyribosil-ribitol-phosphate (anti-PRP IgG); 5 EL.U/ml for anti-FHA, anti-PRN, anti-PT; ≥0.1 IU/ml anti-tetanus toxoid (anti-TT). Only at one month after the third dose (Month 3) in all subjects for: anti-D, anti-HBs and anti-polio 1, 2 and 3. Using ELISA assays with cut-offs: 0.1 IU/ml for anti-diphtheria (anti-D); ≥10 mIU/ml for antihepatitis B (anti-HBs); and microneutralization test cut-off: 1:8 for anti-polio type 1, 2 and 3 (anti-polio 1, 2 and 3).

Statistical Methods:

The seroprotection/seropositivity rates and geometric mean concentrations/titres (GMCs/GMTs) with 95% confidence intervals (95% CI) were computed per group, for SBA-MenC, anti-PSC, SBA-MenY, anti-PSY, anti-PRP, anti-Tetanus, anti-PT, anti-FHA and anti-PRN prior to and one month after vaccination; for anti-Diphtheria, anti-HBs, anti-Polio 1, anti-Polio 2 and anti-Polio 3 one month after vaccination. Vaccine response (appearance of antibodies in subjects initially seronegative or at least maintenance of antibody concentrations in subjects initially seropositive) with 95% CI for anti-PT, anti-PRN and anti-FHA were also computed one month after vaccination. Reverse cumulative curves for each antibody at Month 3 are also presented. The differences between the Hib-MenCY and the Hib-MenC groups, compared with the Menjugate™ control group were evaluated in an exploratory manner for each antibody, except for SBA-MenY and anti-PSY, in terms of (1) the difference between the Menjugate™ group (minus) the Hib-MenCY and Hib-MenC groups for the percentage of subjects above the specified cut-offs or with a vaccine response with their standardized asymptotic 95% CI, (2) the GMC or GMT ratios of the Menjugate™ group over the Hib-MenCY and Hib-MenC groups with their 95% CI. The same comparisons were done to evaluate the difference between each pair of Hib-MenCY formulations for anti-PRP, SBA-MenC, anti-PSC, SBA-MenY, anti-PSY and anti-TT antibodies.

The overall incidences of local and general solicited symptoms were computed by group according to the type of symptom, their intensity and relationship to vaccination (as percentages of subjects reporting general, local, and any solicited symptoms within the 8 days following vaccination and their exact 95% CI). Incidences of unsolicited symptoms were computed per group. For Grade 3 symptoms, onset hours, medical attention, duration, relationship to vaccination and outcomes were provided. Serious Adverse Events were fully described.

Seroprotection/Seropositivity Rates &GMC/Ts (ATP Cohort for Immunogenicity)

TABLE 9a

Anti-PRP (µg/ml)

| Group | N | % ≥0.15 | LL | UL | ≥1 | LL | UL | GMC | LL | UL |
|---|---|---|---|---|---|---|---|---|---|---|
| Hib MenCY 2.5/5/5 | 67 | 100.0 | 94.6 | 100.0 | 98.5 | 92.0 | 100.0 | 9.01 | 7.25 | 11.21 |
| Hib MenCY 5/10/10 | 67 | 100.0 | 94.6 | 100.0 | 98.5 | 92.0 | 100.0 | 9.49 | 7.72 | 11.65 |
| Hib MenCY 5/5/5 | 70 | 100.0 | 94.9 | 100.0 | 98.6 | 92.3 | 100.0 | 8.08 | 6.53 | 9.98 |
| Hib MenC | 74 | 100.0 | 95.1 | 100.0 | 98.6 | 92.7 | 100.0 | 10.44 | 8.49 | 12.83 |
| Menjugate ™ | 71 | 100.0 | 94.9 | 100.0 | 80.3 | 69.1 | 88.8 | 2.60 | 1.97 | 3.43 |

TABLE 9b

SBA-MenC (Titre)

| Group | N | % ≥1:8 | LL | UL | ≥1:128 | LL | UL | GMT | LL | UL |
|---|---|---|---|---|---|---|---|---|---|---|
| Hib MenCY 2.5/5/5 | 70 | 100.0 | 94.9 | 100.0 | 95.7 | 88.0 | 99.1 | 1005.8 | 773.5 | 1308.0 |
| Hib MenCY 5/10/10 | 67 | 100.0 | 94.6 | 100.0 | 94.0 | 85.4 | 98.3 | 1029.8 | 799.7 | 1326.0 |
| Hib MenCY 5/5/5 | 71 | 100.0 | 94.9 | 100.0 | 94.4 | 86.2 | 98.4 | 906.9 | 691.3 | 1189.8 |
| Hib MenC | 74 | 100.0 | 95.1 | 100.0 | 95.9 | 88.6 | 99.2 | 871.0 | 677.3 | 1120.0 |
| Menjugate ™ | 71 | 100.0 | 94.9 | 100.0 | 100.0 | 94.9 | 100.0 | 3557.6 | 2978.8 | 4248.8 |

TABLE 9c

Anti-PSC (µg/ml)

| Group | N | % ≥0.3 | LL | UL | ≥2 | LL | UL | GMC | LL | UL |
|---|---|---|---|---|---|---|---|---|---|---|
| Hib MenCY 2.5/5/5 | 69 | 100.0 | 94.8 | 100.0 | 100.0 | 94.8 | 100.0 | 21.70 | 18.36 | 25.65 |
| Hib MenCY 5/10/10 | 66 | 100.0 | 94.6 | 100.0 | 100.0 | 94.6 | 100.0 | 27.26 | 23.26 | 31.95 |
| Hib MenCY 5/5/5 | 70 | 100.0 | 94.9 | 100.0 | 100.0 | 94.9 | 100.0 | 19.02 | 16.49 | 21.93 |
| Hib MenC | 74 | 100.0 | 95.1 | 100.0 | 100.0 | 95.1 | 100.0 | 21.08 | 18.24 | 24.35 |
| Menjugate ™ | 71 | 100.0 | 94.9 | 100.0 | 100.0 | 94.9 | 100.0 | 38.49 | 33.64 | 44.05 |

TABLE 9d

SBA-MenY (Titre)

| Group | N | % ≥1:8 | LL | UL | ≥1:128 | LL | UL | GMT | LL | UL |
|---|---|---|---|---|---|---|---|---|---|---|
| Hib MenCY 2.5/5/5 | 69 | 97.1 | 89.9 | 99.6 | 92.8 | 83.9 | 97.6 | 470.7 | 351.1 | 631.2 |
| Hib MenCY 5/10/10 | 66 | 97.0 | 89.5 | 99.6 | 86.4 | 75.7 | 93.6 | 437.1 | 322.0 | 593.4.8 |
| Hib MenCY 5/5/5 | 71 | 98.6 | 92.4 | 100.0 | 95.8 | 88.1 | 99.1 | 635.3 | 501.5 | 804.8 |
| Hib MenC | 74 | 21.6 | 12.9 | 32.7 | 13.5 | 6.7 | 23.5 | 9.3 | 6.3 | 13.7 |
| Menjugate ™ | 71 | 19.7 | 11.2 | 30.9 | 9.9 | 4.1 | 19.3 | 7.5 | 5.4 | 10.4 |

TABLE 9e

Anti-PSY (μg/ml)

| Group | N | % ≥0.3 | LL | UL | ≥2 | LL | UL | GMC | LL | UL |
|---|---|---|---|---|---|---|---|---|---|---|
| Hib MenCY 2.5/5/5 | 69 | 100.0 | 94.8 | 100.0 | 100.0 | 94.8 | 100.0 | 26.86 | 22.86 | 31.56 |
| Hib MenCY 5/10/10 | 66 | 100.0 | 94.6 | 100.0 | 100.0 | 94.6 | 100.0 | 37.02 | 31.84 | 43.04 |
| Hib MenCY 5/5/5 | 70 | 100.0 | 94.9 | 100.0 | 100.0 | 94.9 | 100.0 | 23.57 | 19.94 | 27.86 |
| Hib MenC | 74 | 8.1 | 3.0 | 16.8 | 4.1 | 0.8 | 11.4 | 0.19 | 0.15 | 0.25 |
| Menjugate ™ | 71 | 5.6 | 1.6 | 13.8 | 1.4 | 0.0 | 7.6 | 0.17 | 0.15 | 0.19 |

TABLE 9e

Anti-tetanus (IU/ml)

| Group | N | % ≥0.1 | LL | UL | GMC | LL | UL |
|---|---|---|---|---|---|---|---|
| Hib MenCY 2.5/5/5 | 68 | 100.0 | 94.7 | 100.0 | 3.06 | 2.63 | 3.55 |
| Hib MenCY 5/10/10 | 67 | 100.0 | 94.6 | 100.0 | 3.25 | 2.88 | 3.68 |
| Hib MenCY 5/5/5 | 70 | 100.0 | 94.9 | 100.0 | 2.97 | 2.59 | 3.41 |
| Hib MenC | 74 | 100.0 | 95.1 | 100.0 | 3.15 | 2.73 | 3.64 |
| Menjugate ™ | 71 | 100.0 | 94.9 | 100.0 | 1.66 | 1.39 | 1.97 |

Group Hib-MenCY 2.5/5/5: Hib-MenCY (2.5/5/5) + Infanrix ™ penta
Group Hib-MenCY 5/10/10: Hib-MenCY (5/10/10) + Infanrix ™ penta
Group Hib-MenCY 5/5/5: Hib-MenCY (5/5/5) + Infanrix ™ penta
Group Hib-MenC: Hib-Men (5/5) + Infanrix ™ hex
Group Menjugate: Menjugate ™ + Infanrix ™ penta
N = number of subjects with available results.
% = percentage of subjects with concentration/titre within the specified range
GMC/T: geometric mean concentration/titre 95% CI = 95% confidence interval;
LL = Lower Limit;
UL = Upper Limit

CONCLUSION

The immune responses against Hib and MenC were superior using the two formulations with reduced doses of Hib. For MenY, an improved SBA response was seen using the 2.5/5/5 and 5/10/10 formulations compared to the 5/5/5 formulation.

The invention claimed is:
1. A process for making an immunogenic composition, said immunogenic composition comprising:
   a *Haemophilus influenza* type b (Hib) saccharide conjugate;
   an *N. meningitidis* capsular saccharide conjugate derived from a strain selected from the group consisting of serogroups A, B, C, W135 and Y;
   whole cell pertussis; and
   hepatitis B surface antigen;
   the method comprising;
   mixing the Hib saccharide conjugate with at least one *N meningitidis* capsular saccharide conjugate and with the whole cell pertussis and hepatitis B surface antigen to form a composition wherein the saccharide dose of the Hib saccharide conjugate is less than 5 ug and the saccharide does of the *N. meningitidis* capsular saccharide conjugate is less than 8 μg, and wherein the Geometric Mean Concentration (GMC) for whole cell pertussis or hepatitis B achieved with said immunogenic composition is higher than the GSM achieved after immunisation with said immunogenic composition containing a 5 μg saccharide dose of Hib saccharide conjugate and a 8 μg dose of a *N. meningitidis* capsular saccharide conjugate.

\* \* \* \* \*